United States Patent
Poncet

(10) Patent No.: US 8,246,621 B2
(45) Date of Patent: Aug. 21, 2012

(54) REAMER GUIDE FOR REVISION PROCEDURE

(75) Inventor: Didier Poncet, Bron (FR)

(73) Assignee: Depuy (IRELAND) (IE)

( * ) Notice: Subject to any disclaimer, the term of this patent is extended or adjusted under 35 U.S.C. 154(b) by 998 days.

(21) Appl. No.: 12/110,919

(22) Filed: Apr. 28, 2008

(65) Prior Publication Data

US 2009/0270867 A1   Oct. 29, 2009

(51) Int. Cl.
*A61B 17/00* (2006.01)
(52) U.S. Cl. ............... 606/79; 606/80; 606/82
(58) Field of Classification Search .......... 606/79, 606/80, 81, 86 R, 87
See application file for complete search history.

(56) References Cited

U.S. PATENT DOCUMENTS

| 4,998,937 | A | * | 3/1991 | Grimes | 606/89 |
| 5,336,226 | A | * | 8/1994 | McDaniel et al. | 606/79 |
| 5,417,695 | A | * | 5/1995 | Axelson, Jr. | 606/89 |
| 5,480,453 | A | * | 1/1996 | Burke | 623/23.21 |
| 6,120,507 | A | * | 9/2000 | Allard et al. | 606/80 |

* cited by examiner

*Primary Examiner* — Thomas Barrett
*Assistant Examiner* — Melissa A Golob

(57) ABSTRACT

An instrument kit is provided for reaming bone around a head of a bone, the bone including an implanted epiphysis component. The instrument kit includes a reaming guide and a reamer. The reaming guide is couplable to the epiphysis component and has a first reamer support feature and a second reamer support feature. The reamer is couplable to one of the first reamer support feature and the second support feature to ream bone around the epiphysis component.

8 Claims, 19 Drawing Sheets

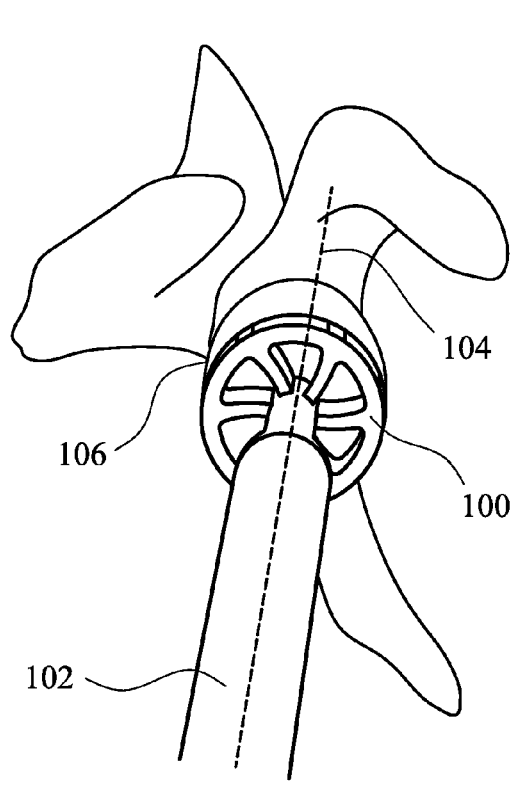
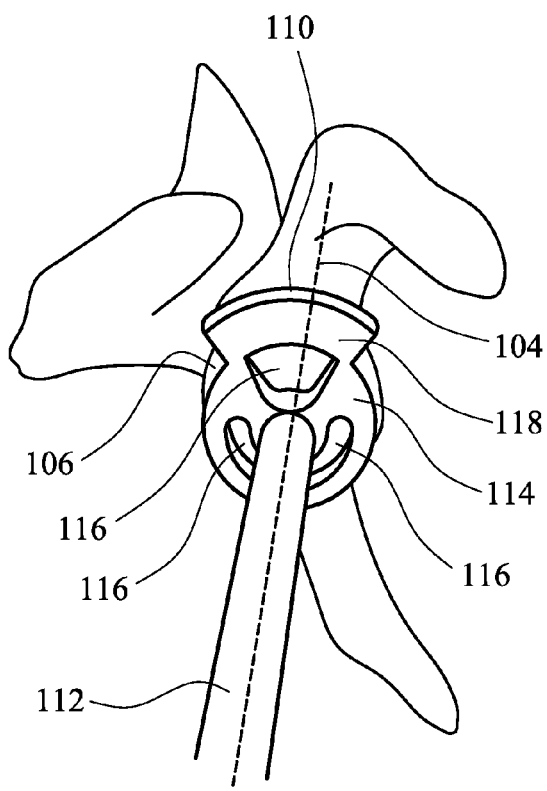
FIG. 10        FIG. 11
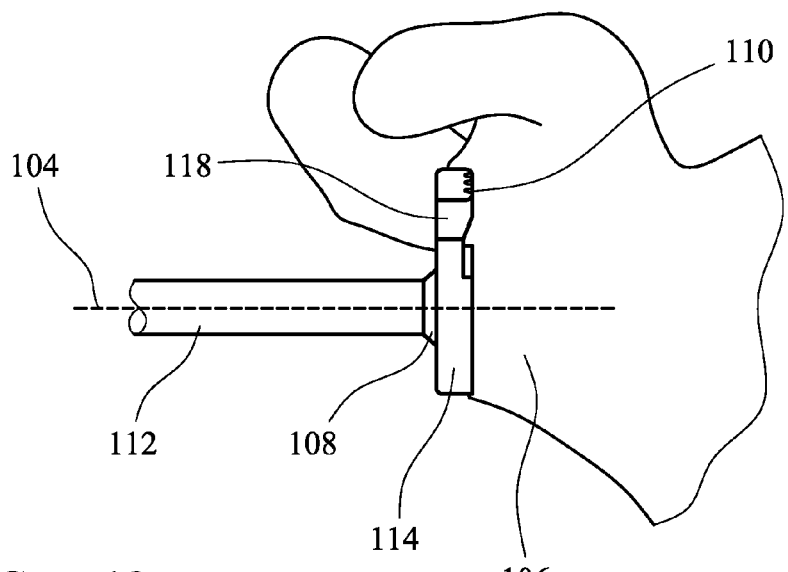
FIG. 12

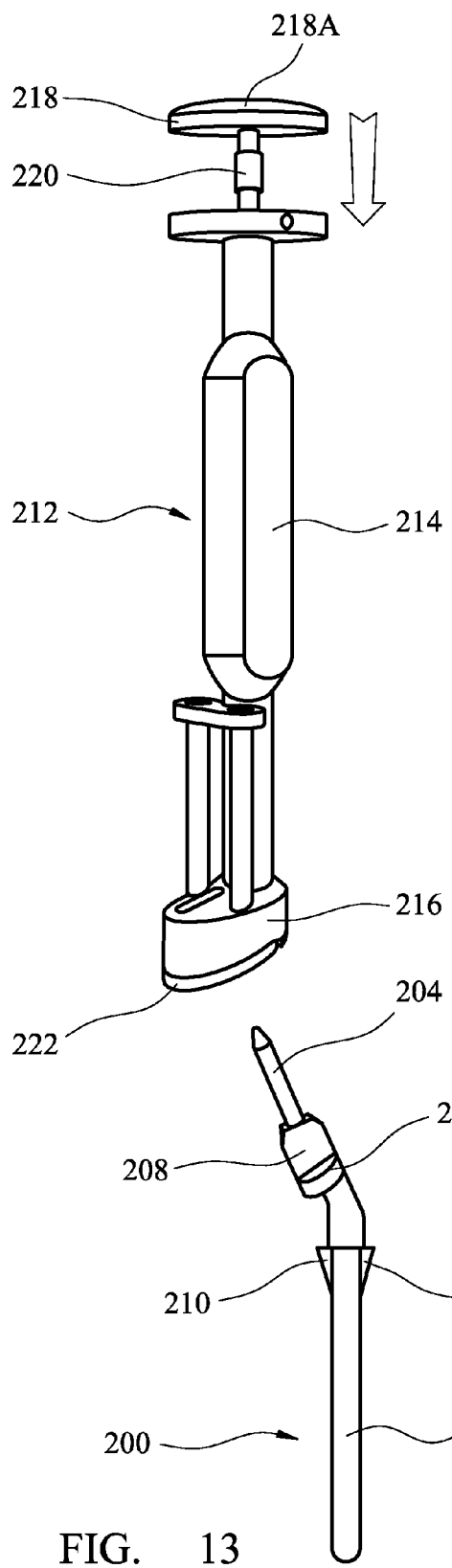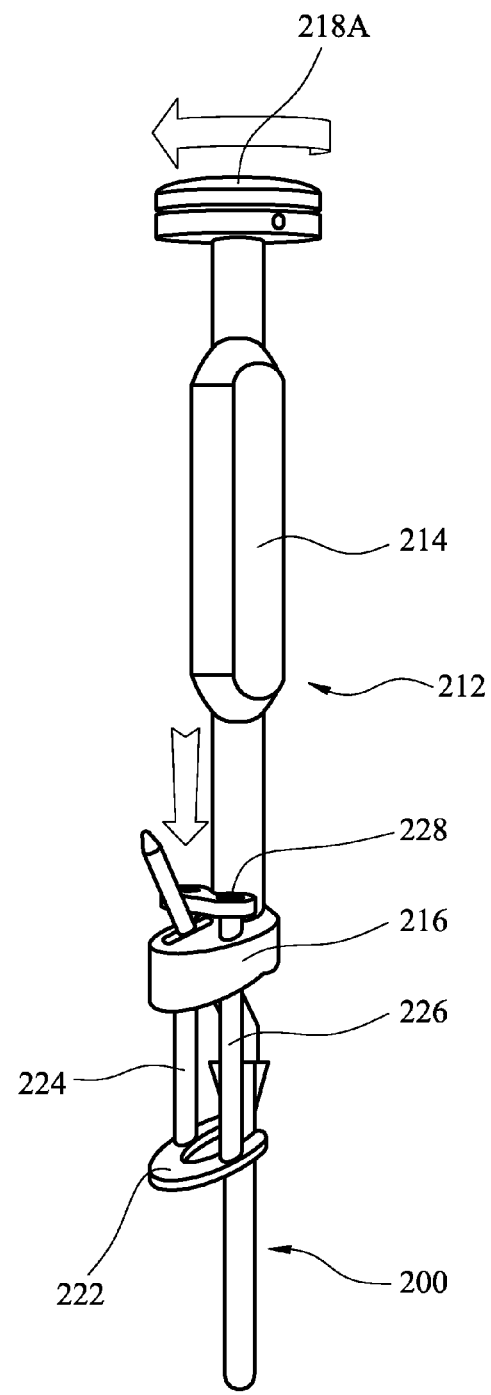
FIG. 13
FIG. 14

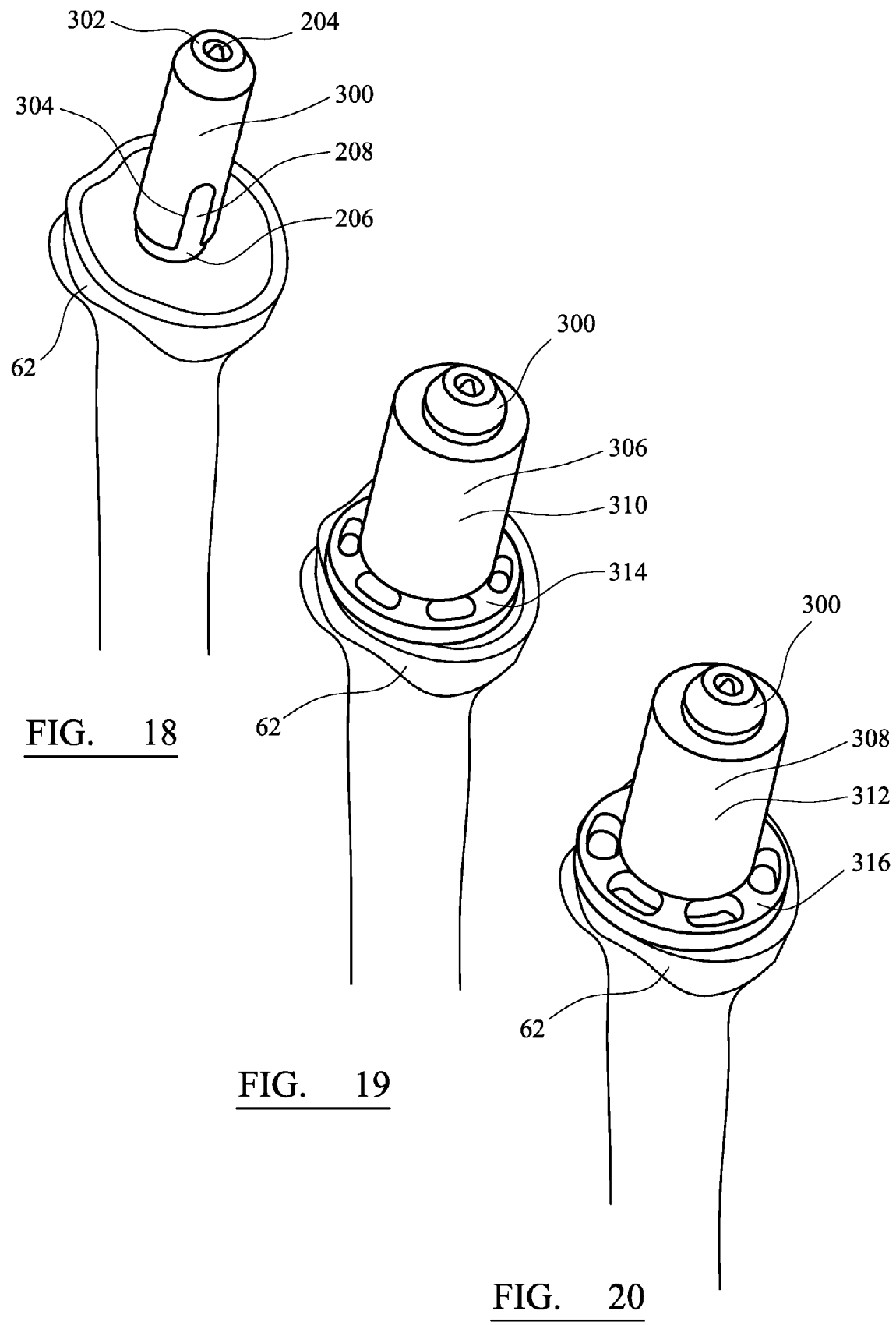

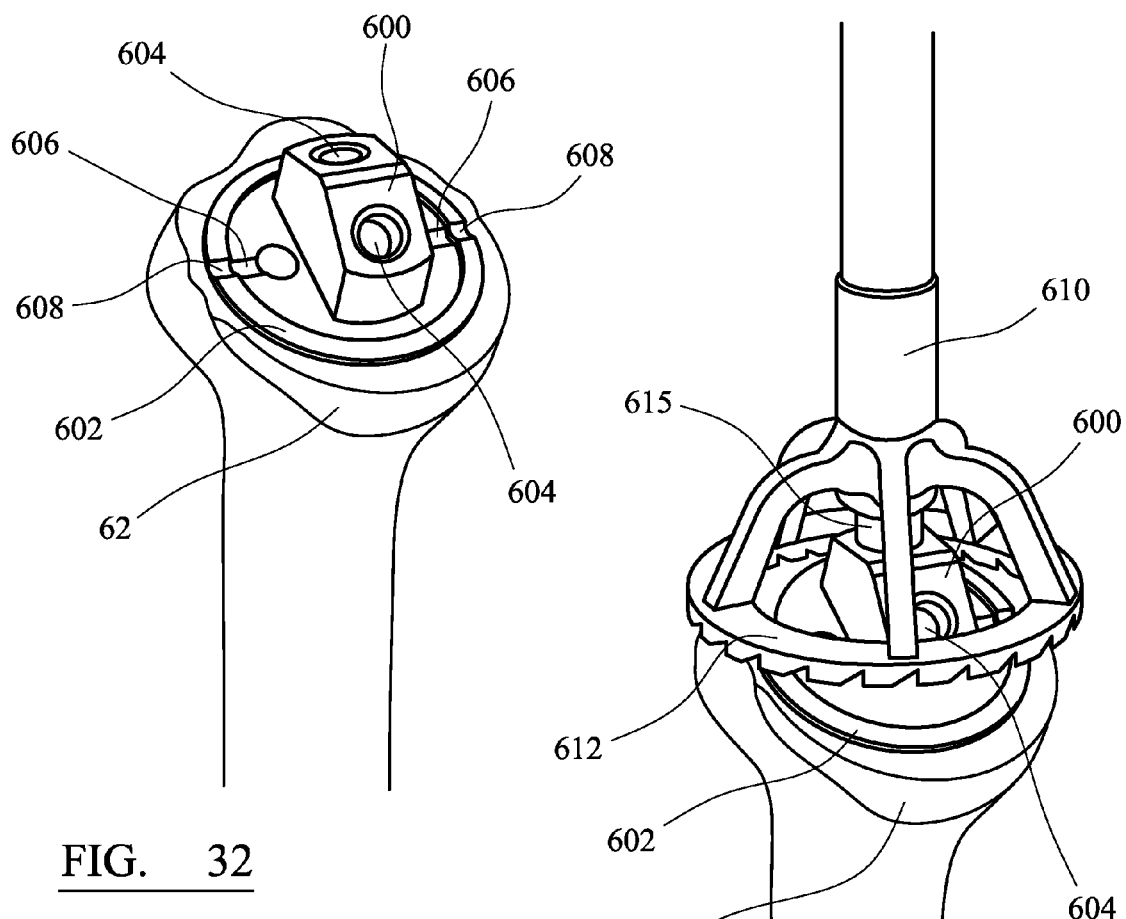
FIG. 32
FIG. 33
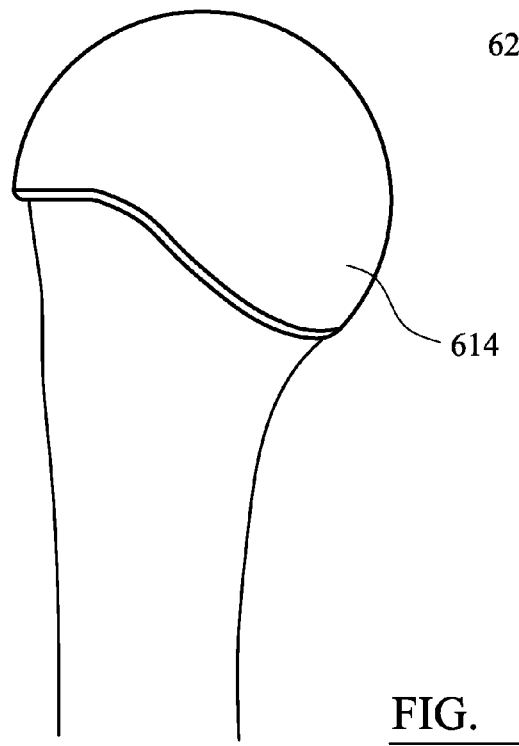
FIG. 34

REAMER GUIDE FOR REVISION PROCEDURE

FIELD OF THE INVENTION

The present invention relates to a surgical instrument. In particular, the present invention relates to a surgical instrument used during a revision procedure in which an implanted reverse shoulder prosthesis is converted to an anatomic figuration. More particularly, the present invention relates to an instrument kit for reaming bone around a head of a bone, the bone including an implanted epiphysis component. The present invention also relates to a method of reaming bone around a head of a bone.

BACKGROUND OF THE INVENTION

A humerus-scapular joint (referred to herein as a shoulder joint) prosthesis comprises a humeral component having a stem part which can be fitted into a reamed cavity within the medullary canal of the humerus, and a glenoid component for attachment to the glenoid. The humeral component and the glenoid component comprise corresponding bearing surfaces which articulate together as the joint moves. In a natural shoulder joint the humeral component comprises a convex head, which articulates against a concave bearing surface on the glenoid. This structure is reproduced in an "anatomic" shoulder joint prosthesis, in which the humeral component includes a stem part and a head part with a convex bearing surface and the glenoid component provides a concave bearing surface. The stem part is implanted within the humerus. The head part is fitted to the stem part, or is formed integrally with the stem part, so that it sits above a resection surface of the humerus. Anatomic prostheses are suitable for implantation in patients where joint tissue has degraded (for example, due to arthritis).

The structure of the anatomic joint is reversed in a "reverse" shoulder joint prosthesis. The glenoid component includes a convex head, and the humeral component has a concave recess in the epiphysis, in which the head on the glenoid component can be received and articulate. The humeral component of a reverse joint prosthesis, including the epiphysis part which provides the bearing surface, may be implanted almost entirely within the humerus.

The biomechanical properties of the patient's joint are altered when a reverse shoulder joint prosthesis is implanted because the center of rotation of the joint is shifted medially. A reverse shoulder joint prosthesis is suitable for implantation in a patient with damaged cuff muscle tissue. The shift of the center of rotation allows manipulation of the arm using the deltoid muscle because of the increased mechanical advantage.

A reverse shoulder prosthesis is described in WO-2007/039820 (DePuy (Ireland) Ltd). Such a joint prosthesis is available commercially and sold by DePuy Products Inc. under the trade name Delta Xtend.

After implantation of a reverse shoulder prosthesis it may be necessary to perform a revision procedure in order to revert the shoulder joint to an anatomic configuration. Alternatively, it may be necessary to revert to an anatomic configuration part way through the implantation of a reverse shoulder prosthesis in the event that it becomes apparent that there is insufficient bone stock to support the reverse shoulder prosthesis. Embodiments of the present invention relate to surgical instruments, and in particular a reaming guide, that may be used during such a revision procedure.

It is an objection of embodiments of the prior art to obviate or mitigate one or more of the problems of the prior art, whether identified herein or elsewhere.

SUMMARY OF THE INVENTION

According to a first aspect of the present invention there is provided an instrument kit for reaming bone around a head of a bone, the bone including an implanted epiphysis component, the instrument kit comprising: a reaming guide couplable to the epiphysis component and comprising a first reamer support feature and a second reamer support feature; and a reamer couplable to one of the first reamer support feature and the second support feature to ream bone around the epiphysis component.

The first reamer support feature may comprise a first socket extending into the reaming guide and the second reamer support feature may comprise a second socket extending into the reaming guide. Each of the first socket and the second socket may be configured to receive a reamer protrusion such that a body of the reamer is held in a fixed spatial relationship with the reaming guide during reaming.

The sockets may define first and second reaming axes that diverge from one another as they extend away from the epiphysis component. The reamer protrusion may comprise an axial guide. The reamer may further comprise a reaming head extending about the axial guide such that the reamer is arranged to ream bone in a concentric ring about the first or the second socket. In use, each reaming axis may diverge from a longitudinal axis of the bone as the reaming axes extend away from the epiphysis component. In use, the reaming axes may be inclined to the longitudinal axis of the bone and extend medially and laterally. The reamer may be configured to ream bone preferentially about medial and lateral sides of the head of the bone.

The reaming guide may be generally disc-shaped and configured to be received within a corresponding socket within the epiphysis component at a resection surface of the bone.

The reaming guide may further comprise an alignment feature configured to be aligned with a corresponding epiphysis component alignment feature.

According a second aspect of the present invention there is provided a method of reaming bone around a head of a bone, the bone including an implanted epiphysis component, the method comprising the steps of: coupling a reaming guide to the epiphysis component, the reaming guide comprising first and second reamer support features; coupling a reamer to one of the reamer support features; and reaming bone around the epiphysis component.

The reamer support features may comprise a first socket and a second socket, each socket extending into the reaming guide. The reamer may comprise a reamer protrusion. The method may further comprise the step of inserting the reamer protrusion into one of the first socket and the second socket such that a body of the reamer is held in a fixed spatial relationship with the reaming guide during reaming.

The first socket and the second socket may define, respectively, a first reaming axis and a second reaming axis that diverge from one another. The reamer protrusion may comprise an axial guide. The reamer may further comprise a reaming head extending about the axial guide, wherein the reaming step comprises reaming bone around the epiphysis component in a concentric ring about the first socket or the second socket.

The reaming guide may be generally disc-shaped, and the coupling step may comprise inserting the reaming guide into one of the first socket or the second socket. The reaming guide may further comprise an alignment feature. The method may further comprise the step of aligning the alignment feature with a corresponding epiphysis component alignment feature.

BRIEF DESCRIPTION OF THE INVENTION

The present invention will now be described, by way of example only, with reference to the following figures, in which:

FIG. 10 illustrates a first reamer being used to ream portions of a glenoid such that a glenoid component of a reverse shoulder prosthesis can be attached to the glenoid;

FIG. 11 illustrates a second reamer being used to ream portions of a glenoid such that a glenoid component of a reverse shoulder prosthesis can be attached to the glenoid;

FIG. 12 illustrates the reamer of FIG. 11 in a side view positioned against the reamed glenoid;

FIG. 13 illustrates an intramedullary reaming guide and an alignment instrument for aligning the intramedullary reaming guide relative to a resected humeral head when the intramedullary reaming guide is inserted into a cavity reamed in the medullary canal of the humerus;

FIG. 14 illustrates the intramedullary reaming guide and the alignment instrument of FIG. 13 coupled together;

FIG. 18 illustrates a centered reaming adapter coupled to a intramedullary reaming guide implanted into a cavity reamed in the medullary canal of the humerus as illustrated in FIG. 17;

FIGS. 19 and 20 illustrate first and second sizing guides respectively coupled to the centered reaming adapter illustrated in FIG. 18;

FIG. 32 illustrates a reaming guide coupled to the epiphysis of the humeral component of a reverse shoulder prosthesis for use within a revision procedure to remove cortical bone around the epiphysis;

FIG. 33 illustrates a reaming head coupled to the reaming guide of FIG. 32; and

FIG. 34 illustrates a humeral head implant couple to a humeral head after reaming using the reaming head of FIG. 33.

DETAILED DESCRIPTION OF EMBODIMENTS OF THE INVENTION

Figure 1:
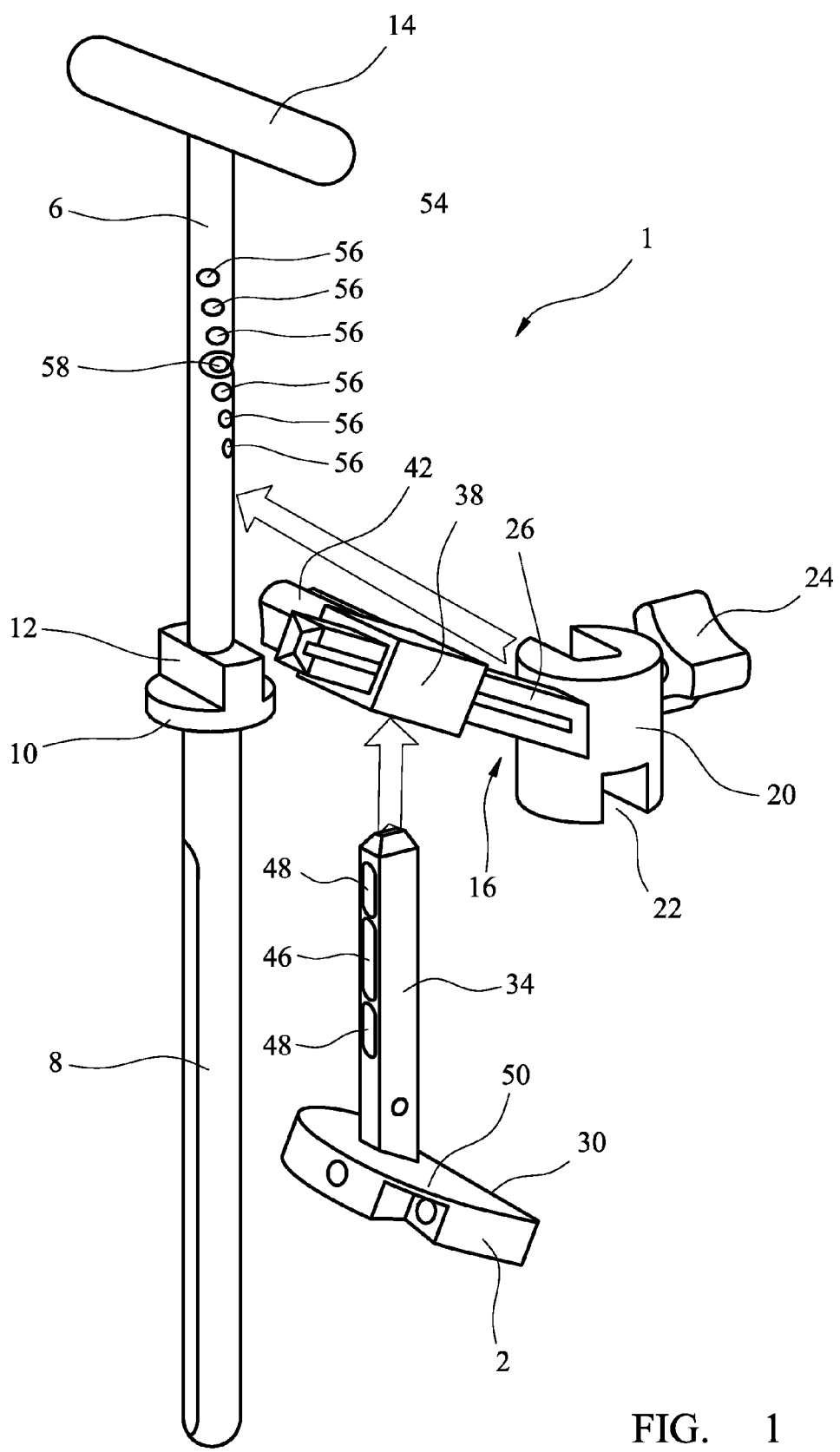
FIG. 1 illustrates in an exploded view a cutting guide for guiding a cutting tool used to resect the head of a humerus, the cutting guide being arranged to be used when a superior-lateral surgical approach exposes the humerus.

A reverse shoulder prosthesis may be of the form available commercially and sold by DePuy Products Inc. under the trade name Delta Xtend Reverse Shoulder System. Such a reverse shoulder system particularly suitable for treating shoulder cuff tear arthropathy. The normal biomechanics of a patient's scapula and humeral components are reversed. Advantageously, the gleno-humeral joint center of rotation is moved medially and inferiorly increasing the deltoid lever arm and the deltoid tension thus allowing the muscles of the deltoid group to compensate for rotator cuff deficiency.

A reverse shoulder prosthesis comprises two primary components: a humeral component implanted into a reamed cavity within the medullary canal of a resected humeral head and a glenoid component attached to a reamed portion of the glenoid part of the scapula. The humeral component may either comprise a modular humeral stem part and an epiphysis part or a single integral component comprising both a humeral stem and an epiphysis. The modular humeral component is preferably designed to form a press fit in a reamed humeral cavity. The integral humeral component is preferably designed to be cemented in position. For press fit humeral components the surface of the implant may be coated with a material which encourages bone in growth thereby securing the implant in position, for instance hydroxyapatite (HA) coated titanium alloy. The glenoid component may be secured primarily by screws into the glenoid with a HA coating for secondary fixation.

The stem part of the humeral component may be similar in form to the stem part of an anatomic shoulder prosthesis. For a modular humeral component it is known for the epiphysis part to be either centered upon the humeral component or offset in a posterior direction to allow for adjustable retroversion, thereby allowing for increased internal rotation of the joint. The plane of the upper face of the epiphysis part is typically at 155° to the axis of the stem part, which increases the stability of the implanted prosthesis.

The glenoid component comprises a mounting plate (alternatively referred to as a metaglene) arranged to be attached to a reamed portion of the glenoid and a convex bearing head (alternatively referred to as a glenosphere) comprising a convex bearing surface mountable upon the mounting plate. The convex bearing head comprises part of a sphere. The convex bearing head may be eccentric (that is, having a fixation hole that is not positioned at the centre of the bearing surface of the convex bearing head) in order to increase the range of motion of the shoulder prosthesis and reduce the risk of scapular erosion.

Between the humeral component and the glenoid component there is provided a humeral cup formed from a material having a low friction surface, such as polyethylene, in order to maximize the range of motion of the shoulder prosthesis and reduce the risk of scapular erosion. The humeral cup is typically coupled to the epiphysis.

In the event of problems arising within implanted reverse shoulder prostheses a reverse shoulder prosthesis can be converted to an anatomical prosthesis. To achieve this, the convex bearing head and the mounting plate are removed from the glenoid and the humeral cup is removed from the epiphysis. A convex bearing head may then be attached to the epiphysis, arranged to articulate against the glenoid and the acromion.

A surgical procedure for implanting a reverse shoulder prosthesis and optionally converting the prosthesis to an anatomic prosthesis, and particular the surgical instruments used in such a procedure will now be described.

Prior to surgery an initial assessment is made of the humerus and the glenoid using radiographic and CT imaging to determine whether there is sufficient bone stock for implantation of the humeral component and the glenoid component. If the patient is suitable for treatment, then the imaging may be measured in order to determine the appropriate size of implants, though the final decision is typically left to the surgeon's discretion.

A reverse shoulder prosthesis may be implanted using a surgical approach involving either a superior-lateral incision or a deltoid-pectoral incision. The decision is subject to the surgeon's preference and clinical parameters. The chosen approach affects the surgical instruments and techniques used, in particular the instruments used for resecting the humeral head, as will be described in greater detail below.

A superior-lateral approach comprises forming an incision either anterior-posterior along the lateral edge of the acromion or in a lateral direction starting from a superior position on the shoulder. The shoulder is dissected until the humeral head is visible at the anterior edge of the acromion. The arm may then be externally rotated and the head dislocated antero-superiorly to facilitate positioning of a cutting guide. The superior-lateral approach allows for a clear view of the glenoid and therefore facilitates the implantation of the glenoid implant components, in particular when the glenoid is retroverted.

A deltoid-pectoral approach comprises forming an incision from the midpoint of the clavicle to the midpoint of the arm. The shoulder is dissected until the humeral head is visible and can be dislocated. The deltoid-pectoral approach has the advantage of offering an enhanced view of the inferior part of the glenoid. If revision surgery is required in order to convert the humerus-scapula joint to an anatomical configuration the deltoid-pectoral approach is preferred as it allows for a longer humeral incision.

Regardless of the surgical approach, once the humeral head is visible and has been dislocated the first step is to form an intramedullary cavity. The cavity runs from the humeral head parallel to the longitudinal axis of the humerus. The cavity defines a longitudinal axis extending along the cavity into the humerus. A pilot hole must first be drilled into the humeral head, passing directly down into the medullary canal along the bone. A series of hand reamers having progressively larger diameters are then used to enlarge the cavity until there is contact with cortical bone of the intramedullary canal of the humerus. The diameter of the final reamer used determines the size of the cutting guide assembly support rod, intramedullary reaming guide and the final humeral component, as will be described herein. For example, if a 12 mm reamer begins to gain purchase in the intramedullary cortical bone (and so is the largest reamer used) then a 12 mm stem for the humeral component will be required.

Figure 2:
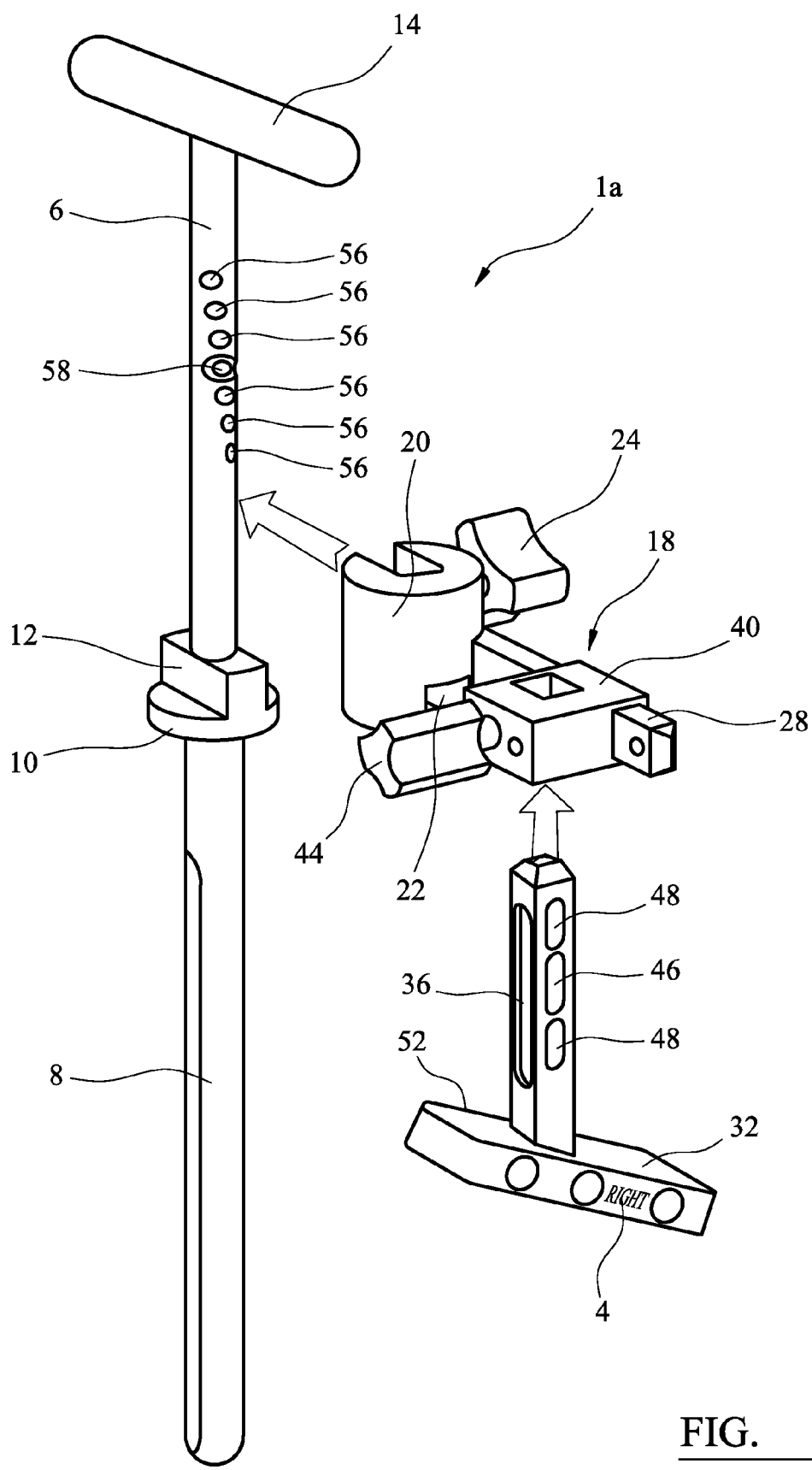
FIG. 2 illustrates in an exploded view a cutting guide for guiding a cutting tool used to resect the head of a humerus, the cutting guide being arranged to be used when a deltoid-pectoral surgical approach exposes the humerus.

Once the intramedullary cavity has been formed, then the humeral head can be resected. Referring to FIGS. 1 and 2 these respectively illustrate in exploded views alternative cutting guide assemblies that may be used to guide a cutting tool for resecting the humeral head. The cutting guide assembly illustrated in FIG. 1, generally referred to as reference numeral 1, is arranged to be used when the surgical approach is superior-lateral, whereas the cutting guide assembly illustrated in FIG. 2, generally referred to as reference numeral 1a, is arranged to be used when the surgical approach is deltoid-pectoral.

The required resection of the humeral head is the same regardless of the surgical approach. The resection surface is typically required to be at an angle of 15° to the longitudinal axis of the humerus defined by the intramedullary cavity. The cutting guide assemblies 1, 1a illustrated in FIGS. 1 and 2 present a cutting surface on a cutting plate that is automatically orientated at 155° to the longitudinal axis of the humerus. The resection surface faces medially and superiorly; that is, it faces towards the glenoid. For a superior-lateral approach the visible portion of the humeral head is predominantly the superior and lateral portions of the humeral head, whereas for a deltoid-pectoral approach it is predominantly the anterior portion of the humeral head that is visible. Consequently, a separate cutting guide assembly is required for each surgical approach. Each cutting assembly is suitable for performing surgical procedures on either a patient's left or right arm. The superior-lateral cutting guide assembly of FIG. 1 may be used for either the right arm (as illustrated) or the left arm by simply rotating the whole assembly. The deltoid-pectoral cutting guide of FIG. 2 may be used for either the right arm (as illustrated) or the left arm by rotating the cutting plate 4. As shown in FIG. 2, the cutting plate 4 is engraved with "RIGHT" on a first side indicating that it is orientated for used on a right shoulder and "LEFT" on a second opposite side (not visible) indicating that it is orientated for use on a left shoulder. It will be apparent from the description below that the cutting guide assemblies 1, 1a comprise a selection of modular components, some of which are common to each surgical approach. FIGS. 1 and 2 illustrate cutting guide assemblies 1, 1a suitable for resecting the head of a right humerus of a patient.

Each cutting guide assembly 1, 1a comprises a cutting plate 2, 4 illustrated in FIGS. 1 and 2 respectively. Each cutting plate comprises a cutting surface that defines the resection surface, and may be maneuvered until it is in the optimal position for performing the resection. The resection is then achieved by the surgeon aligning a cutting tool with the cutting surface such that the resection surface is parallel to the cutting surface of the cutting plate.

The cutting guide assemblies 1, 1a illustrated in FIGS. 1 and 2 each comprise the same support rod 6. The support rod 6 comprises an elongate rod including a first portion 8 for insertion into the reamed intramedullary cavity. Each cutting guide assembly is provided with a range of support rods 6, with each support rod 6 being provided with a different diameter first portion 8 corresponding to the differing diameters of the reamers used to form the intramedullary cavity. For instance, if a 12 mm intramedullary cavity has been formed then a 12 mm diameter support rod 6 must be used to ensure that the support rod 6 forms a close fit in the intramedullary cavity.

Each support rod 6 comprises a flange 10 which forms a depth stop preventing over insertion of the support rod 6 into the intramedullary cavity by coming to rest against the top surface of the humeral head. Adjacent to the flange 10 the support rod 6 further comprises a reference formation 12. The reference formation 12 is formed as a rib. The orientation of the reference formation 12 relative to the longitudinal axis of the humerus determines the orientation of the resection surface about the longitudinal axis of the humerus. The support rod 6 further comprises a T shaped handle 14 which may be manipulated by a surgeon in order to rotate the support rod 6 within the intramedullary cavity to adjust the orientation of the resection surface, as will be described in greater detail below.

Once the support rod 6 has been fully inserted into the intramedullary cavity the remainder of the cutting guide assembly may be assembled. The cutting guide assemblies 1, 1a illustrated in FIGS. 1 and 2 each comprise a separate cutting plate mount 16, 18 respectively for coupling the cutting plate 2, 4 to the support rod 6. Each cutting plate mount 16, 18 comprises a clamp formed as a collar 20 arranged to surround the shaft of the support rod 6 and engage the reference formation 12. The collar 20 incorporates a groove 22 arranged such that when coupled to rib 12, collar 20 is prevented from rotating about the support rod 6. A locking screw 24 is provided, which passes through a corresponding hole in the collar 20 and engages the shaft of the support rod 6 holding the collar in place.

The purpose of cutting plate mounts 16, 18 is to position the cutting plates 2, 4 in an appropriate position to define the plane of the resection surface. Consequently, each cutting plate mount 16, 18 further comprises a shaft 26, 28 that extends from the collar 20. Shafts 26, 28 extend from collar 20 along an axis parallel to the plane of the cutting surface of the cutting plate 2, 4 (and hence parallel to the resulting resection surface). For the cutting guide assembly illustrated in FIG. 1 when assembled for a superior-lateral approach of a right shoulder the shaft 26 extends from the collar 20 laterally so as to protrude from the patient's shoulder through the incision. Consequently, in order to lie parallel to the resection surface, shaft 26 extends superiorly and laterally. For the cutting guide illustrated in FIG. 2 when assembled for a deltoid-pectoral approach of a right shoulder the shaft 28 extends from the collar 20 anteriorly so as to protrude from the patient's shoulder through the incision. Consequently, in order to lie parallel to the resection surface, shaft 28 extends perpendicularly from the support rod 6.

Cutting plate 2 illustrated in FIG. 1 is provided with a concave curved edge 30 on the side that in use will be adjacent to the humeral head. Curved edge 30 is intended to reflect the profile of the humeral head so as to allow the cutting plate 2 to be positioned close to the lateral portion of the humeral head. Conversely, cutting plate 4 illustrated in FIG. 2 has a straight edge 32 on the side that in use will be adjacent to the anterior portion of the humeral head. Extending superiorly from each cutting plate 2, 4 and parallel to the axis of the support rod 6 is a post 34, 36. Posts 34, 36 are slidably received within a respective clamp 38, 40, which in turn is slidably mounted upon shafts 26, 28 respectively. The position of the clamps 38, 40 with respect to posts 34, 36 can be locked by tightening screws 42, 44 in order to preserve the height adjustment of the cutting plate 2, 4 selected by the surgeon. Clamps 38, 40 remain free to slide along shafts 26, 28 so that the cutting plate 2, 4 can be slid close to the humerus before being secured in position (as described below).

The arrangement of the cutting plate mounts 16, 18 is such that for each cutting guide assembly the cutting plates 2, 4 may be raised or lowered parallel to the longitudinal axis of support rod 6 by sliding posts 34, 36 through clamps 38, 40. This allows the surgeon to select the appropriate position of the resection surface along the longitudinal axis of the humerus. Posts 34, 36 are provided with color coded markings, comprising a central red marking 46 and outer green markings 48. Normally, the post 34, 36 will be locked in position by the respective clamp 38, 40 such that only the green markings 48 are visible either side of the clamp 38, 40. This ensures that the resection surface is located along the longitudinal axis of the humerus at the correct position for most patients (if the support rod 6 is inserted into the medullary canal sufficiently far for the flange 10 to contact the upper surface of the humeral head). However, on a patient specific basis, the sliding adjustment of posts 34, 36 allows the position of the resection surface along the longitudinal axis of the humerus to be adjusted according to clinical parameters.

Furthermore, the arrangement of the cutting plate mounts 16, 18 is such that for each cutting guide assembly the cutting plates 2, 4 may be brought closer to, or in contact with, the humeral head by sliding clamps 38, 40 along shafts 26, 28. Given that shafts 26, 28 extend parallel to the required resection surface, once the surgeon has selected the appropriate level of the resection surface along the longitudinal axis of the humerus, the cutting plates 2, 4 can be slid towards the humeral head parallel to the resection surface, such that the position of the resection surface is not affected. Bringing the cutting plates into contact with the humeral head advantageously allows the surgeon to cut the humeral head by running the cutting tool along the cutting surface with less risk of inaccuracy caused by stray motion of the cutting tool.

As illustrated in FIGS. 1 and 2, the cutting surface is defined by the superior side 50, 52 of the cutting plates 2, 4. However, as will be appreciated, the arrangement is such that a surgeon would be compelled to cut around posts 34, 36 and also the support rod 6 where it extends into the humeral head. As will be described below, once the cutting plate 2, 4 has been appropriately positioned, the cutting plate 2, 4 can be locked in position on the humeral head and the support rod 6 and the cutting plate mount 16, 18 removed in order to ease a surgeon's work in resecting the humeral head.

As has been described above, the provision of separate cutting guide assemblies 1, 1a optimized for use with either a superior-lateral or a deltoid-pectoral surgical approach allows a surgeon to accurately position a cutting plate 2, 4 (and hence the resection surface) at a desired level along the longitudinal axis of the humerus by adjustment of clamp 38, 40. The desired orientation about the longitudinal axis of the humerus is set by rotation of the support rod 6. The correct angle of the resection surface with respect to the longitudinal axis of the humerus is set automatically by the angle subtended between the cutting plate 2, 4 and post 34, 36, which in use is parallel to the longitudinal axis of cavity and hence parallel to the longitudinal axis of the bone. The cutting guide assemblies 1, 1*a* allow these parameters of the resection surface to be set in a controlled fashion which is not solely dependent upon the surgeon's skill and judgment in order to correctly position the resection surface. The cutting guide assemblies 1, 1*a* allow the position of the resection surface to be finely adjusted before any cutting step is required.

As noted above, the orientation of the resection surface about the longitudinal axis of the humerus can be adjusted by rotating the support rod 6 within the intramedullary cavity. In order to assist the alignment of the resection surface, an upper portion 54 of the support rod 6 further comprises a series of alignment holes 56 which pass through the support rod 6. The alignment holes 56 include a primary alignment hole 58 indicated by a flared entrance hole. As can be seen, the axis of the primary alignment hole is parallel to the axis of the reference formation 12 defined by the long axis of the rib. The remaining alignment holes 56 form a series of alignment holes extending though the support rod 6 at differing radial directions.

Figure 3:
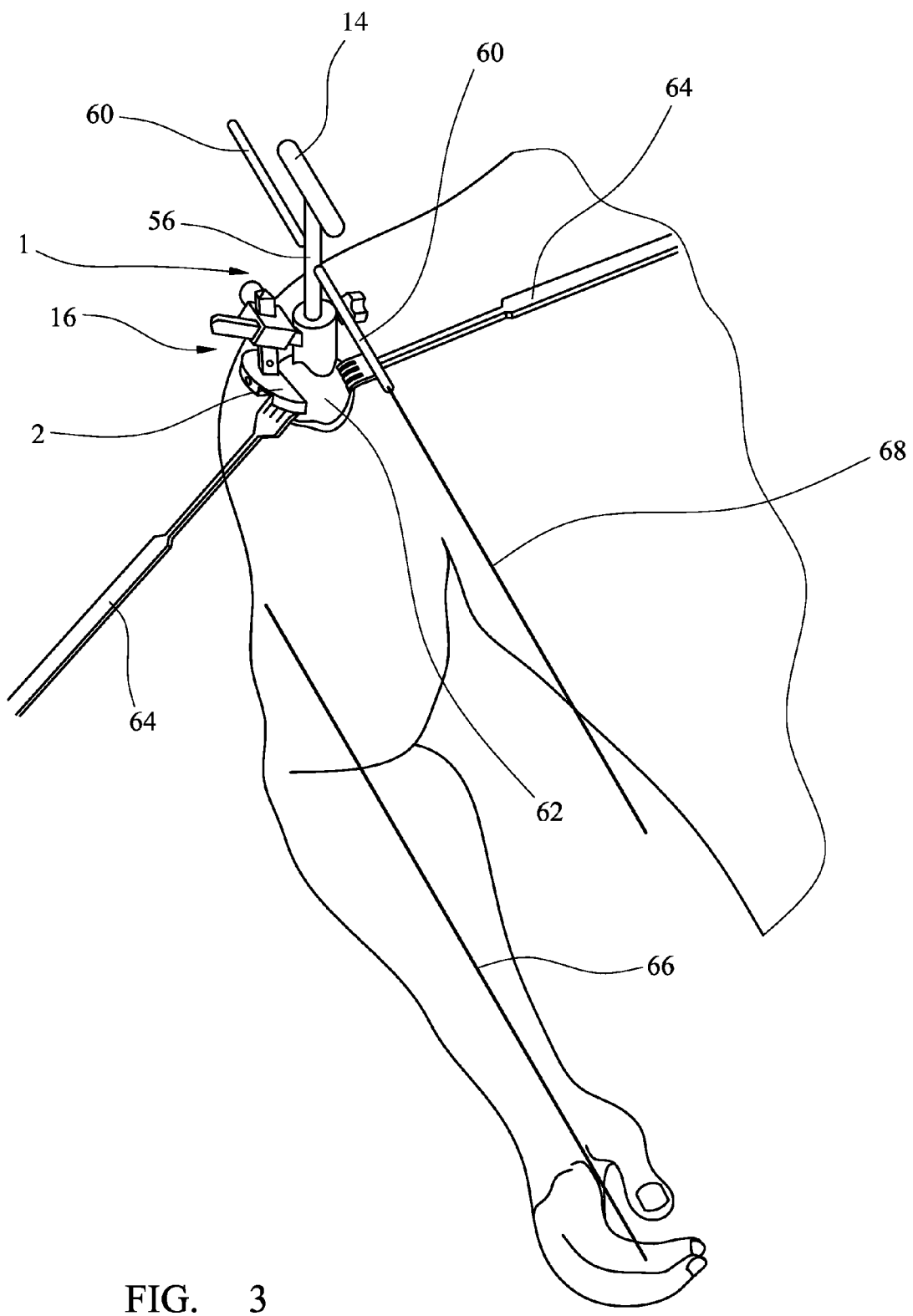
FIG. 3 illustrates the cutting guide of FIG. 1 assembled and in position on the head of a humerus, and illustrating the use of an alignment pin for determining the orientation of the cutting guide.

When the support rod 6 is inserted into the intramedullary cavity, an alignment rod 60 can be inserted into one of the alignment holes 56 and use to rotationally align the cutting guide handle 6, as is shown in FIG. 3. FIG. 3 shows a cutting guide in accordance with FIG. 1 being used to locate cutting plate 2 relative to a humeral head 62 when the humeral head 62 has been exposed using a superior-lateral surgical approach. Soft tissue of the patients shoulder is shown held back by retractors 64. It will be appreciated that an alignment rod 60 may be used to align the cutting guide of FIG. 2 in the same way, given that the support rod is the same for each cutting guide.

Adjusting the rotational position of the resection surface varies the degree of retroversion or anteversion (that is the rotational position about the longitudinal axis of the humerus of a line which is normal to the resection surface and intersects the longitudinal axis of the humerus) applied to the implanted reverse shoulder prosthesis. The retroversion or anteversion of the final implant position can be assessed by comparing the axis 68 of the alignment rod 60 with the patient's forearm axis 66. Rotating the support rod 6 within the intramedullary cavity until the alignment rod axis 68 is parallel to the patient's forearm axis 66 ensures that required degree of retroversion or anteversion is set for the resection surface. If the alignment pin 60 is inserted into the primary alignment hole 58 then 0° retroversion is set for the resection surface. If alternatively one of other alignment holes 56 are used then a predetermined degree of retroversion or anteversion can be provided to the resection surface. Typically 0-10° retroversion is applied since excessive retroversion can restrict joint mobility, especially internal rotation. However, care must be taken not to damage the subscapularis insertion by resecting the humeral head 62 with excessive anteversion.

Figure 4:
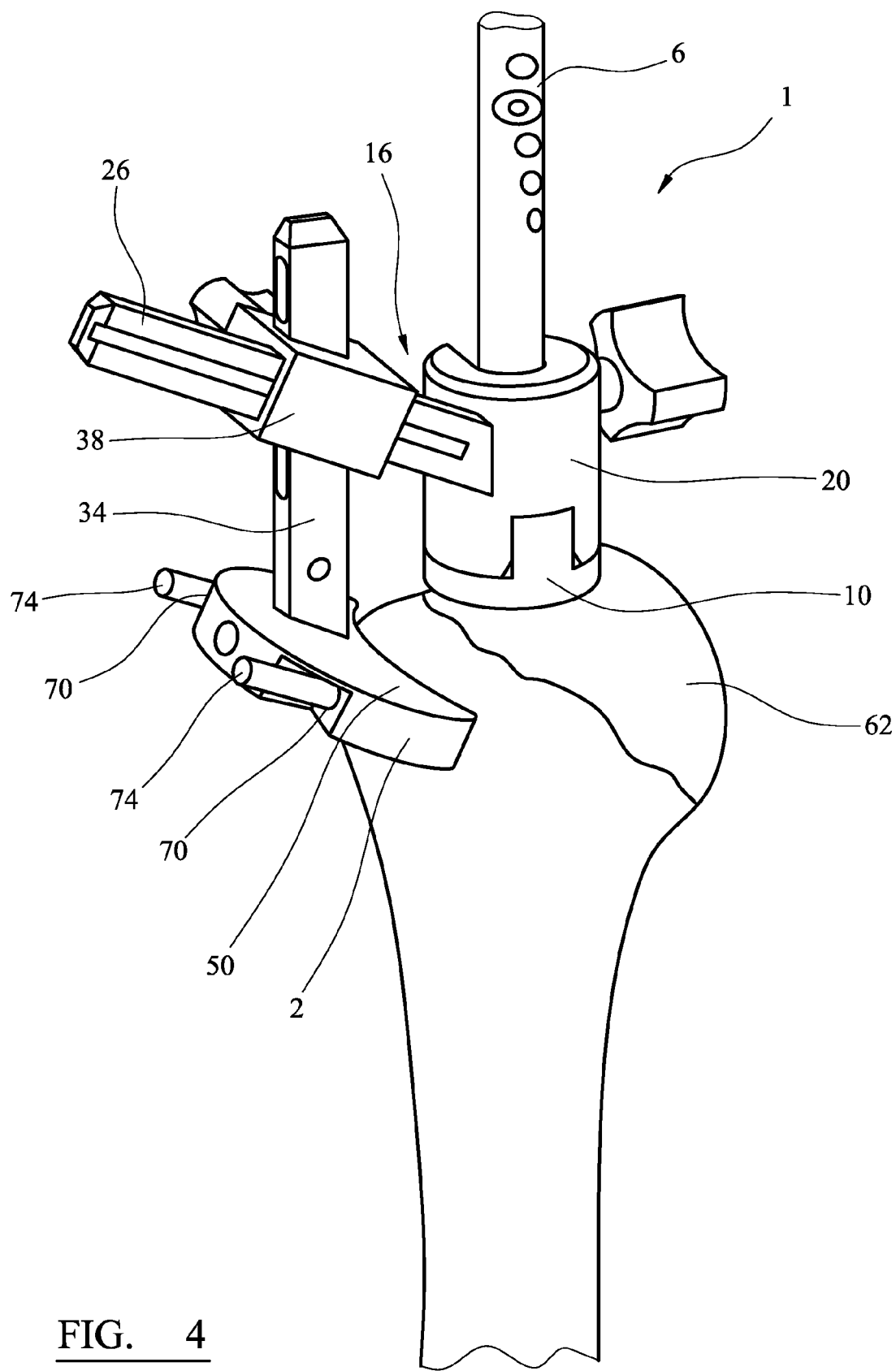
FIG. 4 illustrates the cutting guide of FIG. 1 assembled and in position on the head of a humerus.
Figure 5:
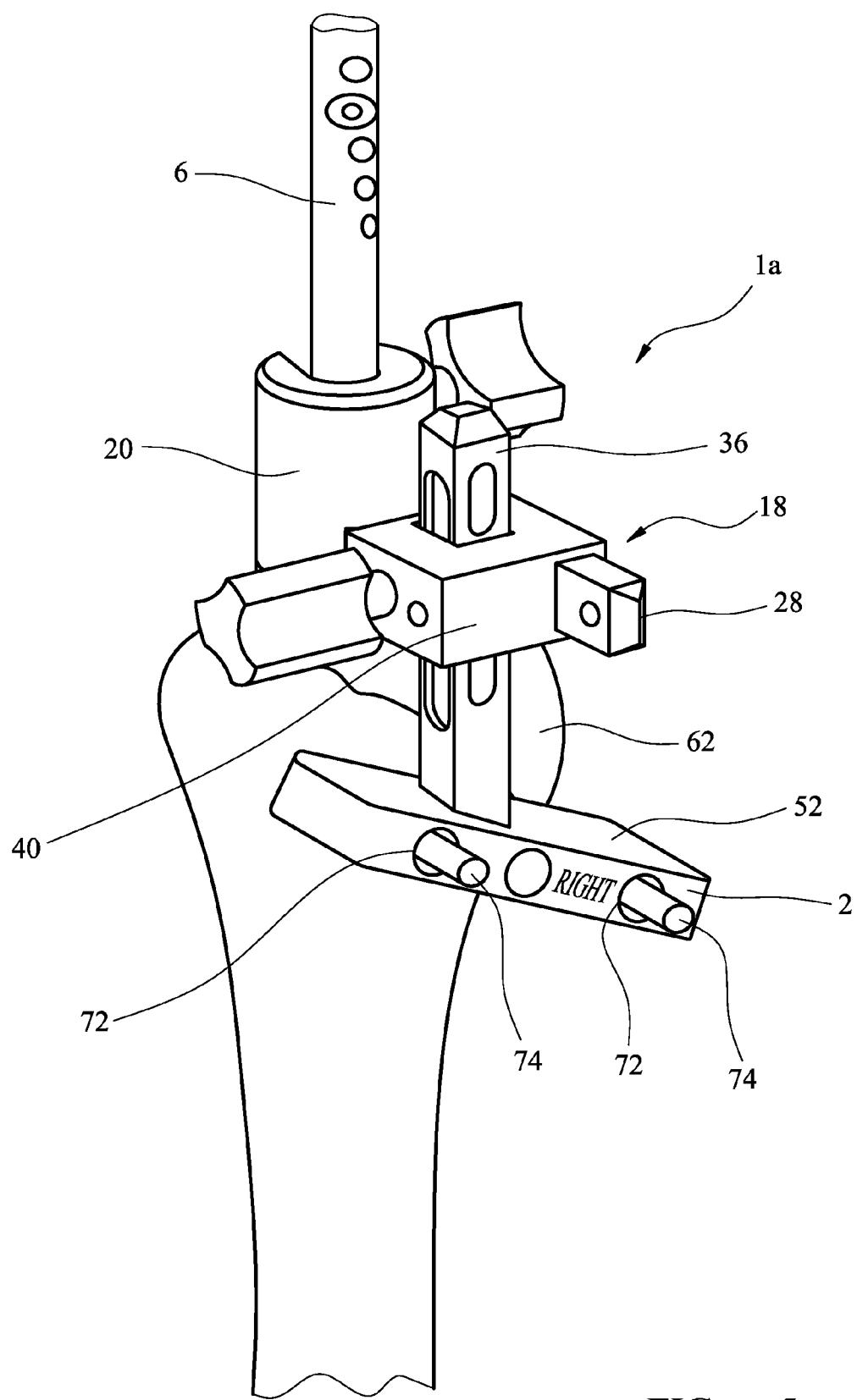
FIG. 5 illustrates the cutting guide of FIG. 2 assembled and in position on the head of a humerus.

Once the desired degree of retroversion or anteversion has been set, the level of the resection surface can be adjusted as discussed above, typically such that only the green markers 48 are visible on post 34. Usually 1-2 mm of the proximal area of the greater tuberosity is resected (at the level of the suprspinatus insertion on an intact shoulder). The cutting plate 2, 4 can then be slid into contact with the humeral head 62 by adjusting the position of the clamp 38, 40 along shaft 26, 28. FIGS. 4 and 5 show the cutting guide assemblies 1, 1*a* illustrated in FIGS. 1 and 2 respectively assembled and positioned upon a humeral head 62 such that the cutting surface 50, 52 is positioned defining the plane of the chosen resection surface. For clarity, soft tissue surrounding the humeral head 62 is not shown.

As noted above, the cutting plate 2, 4 may be secured to the humeral head 62 such that the remainder of the cutting guide assembly can be removed, assisting the surgeon in resecting the humeral head 62 by passing a cutting tool over the cutting surface 50, 52. As shown in FIGS. 4 and 5, each cutting plate 2, 4 further comprises a pair of guide holes 70, 72 respectively at each end of the cutting plate 2, 4. Once the cutting plate 2, 4 is correctly positioned, holes may be drilled through the guide holes 70, 72 into the cortical bone with a 3.2 mm drill bit, using the cutting plate 2, 4 as a drill guide. Fixation pins 74 may then be passed through the guide holes 70, 72 preserving the alignment of the cutting plate 2, 4 relative to the humeral head 62.

Figure 6:
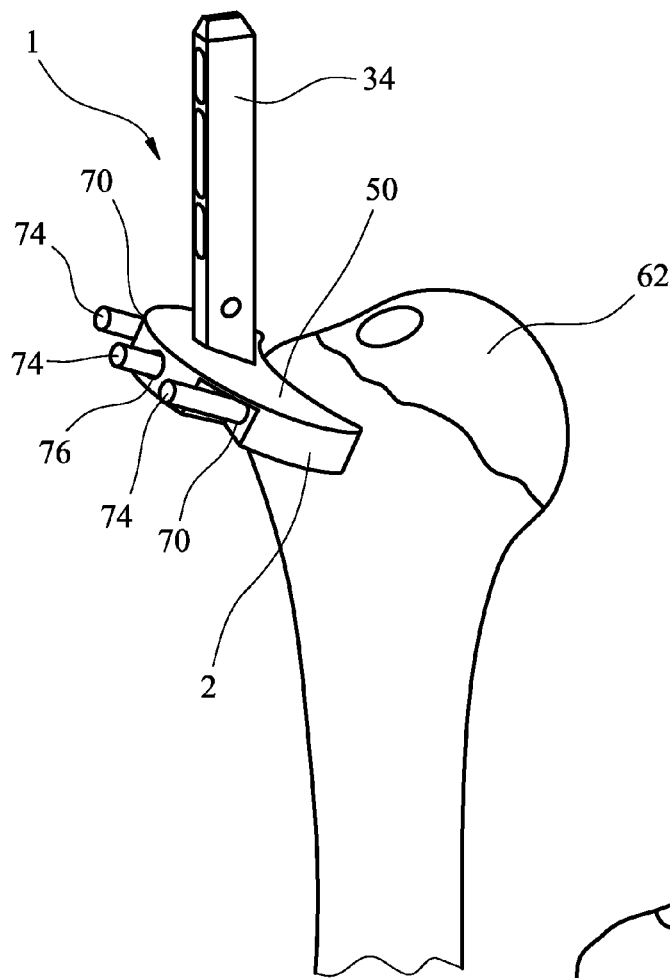
FIGS. 6 and 8 illustrate a cutting plate forming part of the cutting guide of FIG. 1 attached to the head of a humerus in first and second configurations.
Figure 7:
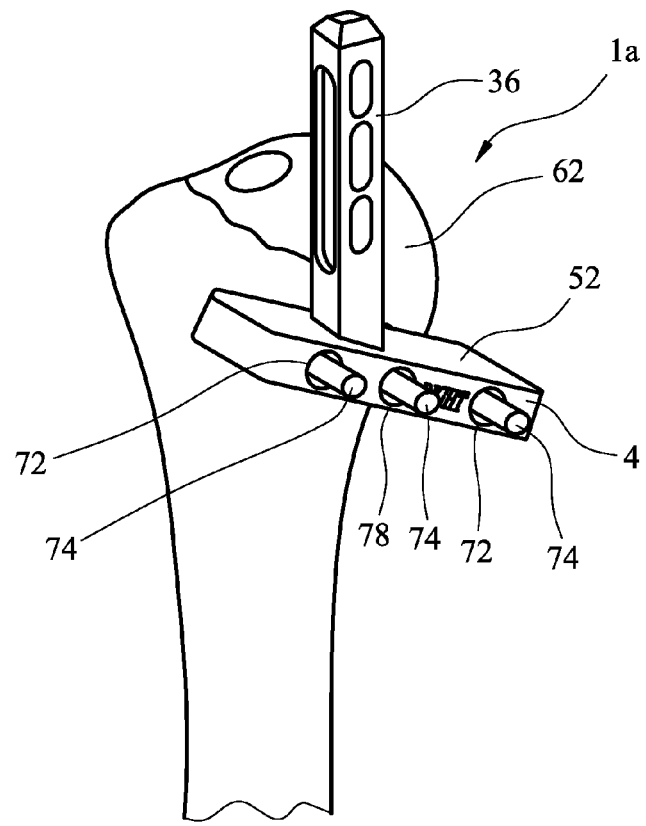
FIGS. 7 and 9 illustrate a cutting plate forming part of the cutting guide of FIG. 2 attached to the head of a humerus in first and second configurations.

Once fixation pins 74 are in position, the cutting plate mount 16, 18 can be removed from the cutting plate 2, 4 by slackening off locking screw 42, 44 thereby freeing post 34, 36 which extends from the cutting plate 2, 4. Slackening off locking screw 24 allows the clamp 20 to be lifted parallel to the longitudinal axis of the support rod 6 such that cutting plate mount 16, 18 is decoupled from the cutting plate 2, 4 without disturbing its position relative to the humeral head 62. The support rod 6 can then be released from the intramedullary cavity. The cutting plate 2, 4 is supported on the humeral head 62 by the fixation pins 74 as shown in FIGS. 6 and 7 in the relative position determined through the above alignment steps. The cutting plate 2, 4 can be further secured to the humeral head 62 by passing a third fixation pin 74 through a third guide hole 76, 78. The outer pair of guide holes 70, 72 are arranged to be parallel to one another such that the cutting plate 2, 4 can slide along fixation pins 74 towards and away from the humeral head parallel to the resection surface 50, 52. The third, central guide hole 76, 78 defines an axis which is divergent from the axes of the first two guide holes 70, 72. Consequently, when the third fixation pin 74 is inserted the cutting plate 2, 4 is held firmly in position.

Figure 8:
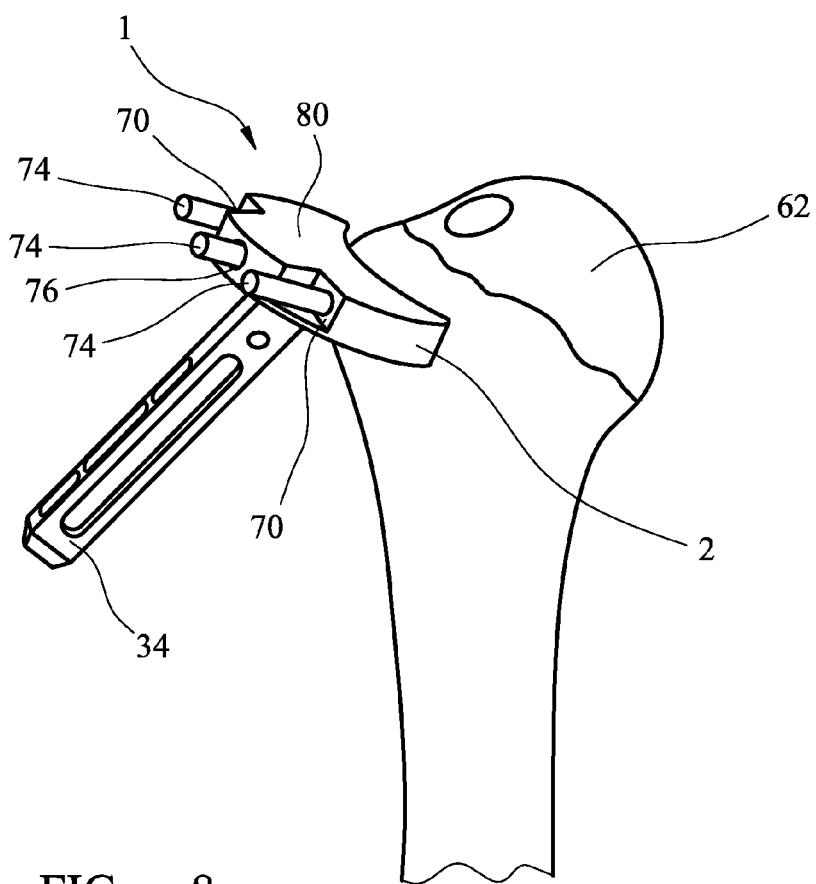
Figure 9:
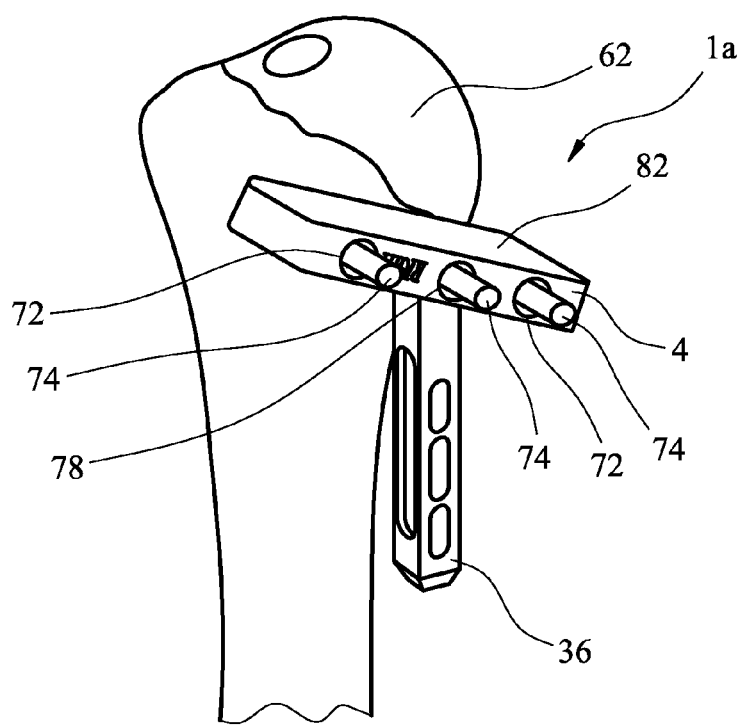

As will be appreciated from FIGS. 6 and 7 the surgeon is able to resect the humeral head 62 by passing a cutting tool parallel to and next to the cutting surface 50, 52. Removal of the other components of the cutting guide assembly greatly reduces the complexity of the cutting step that must be performed by the surgeon. However, post 34, 36 extending from the cutting plate is still in the way of the resection and must be cut around, possibly resulting in a less accurate resection. In order to avoid this obstacle, before the third fixation pin 74 is inserted, the cutting plate 2, 4 can be removed from the initial pair of fixation pins 74 by sliding along the axes of the parallel pair of fixation pin 74. The cutting plate 2, 4 can then be inverted and replaced over the fixation pins 74 as shown in FIGS. 8 and 9. The cutting plate 2, 4 additionally defines a second cutting surface 80, 82, which now faces superiorly and in the plane previously occupied by the first cutting surface 50, 52. Second cutting surface 80, 82 is parallel to the first cutting surface 50, 52 and equidistant from the fixation pins 74. Consequently, the second surface 80, 82 is parallel to the same chosen resection surface. Advantageously, there is no post protruding from the second cutting surface 80, 82 allowing for the resection to be performed as a single cutting action resulting in a more even resection. Again, a third fixation pin 74 can be provided through divergent guide hole 76, 78 securing the cutting plate 2, 4 in position.

It will be appreciated that in alternative embodiments the cutting plate assembly may be varied. In particular, the coupling mechanism to the support rod may be modified to provide alternative mechanisms for coupling the cutting plates such that cutting plates designed for different surgical approaches are aligned to the same desired resection plane. Similarly, the height adjustment of the cutting plate may be modified, for instance by coupling to the cutting plate mount via an alternative connection. It will be desirable that any alternative cutting guide assembly retains the ability for the cutting plate assembly to be disassembled while the cutting plate remains attached to the head of the bone.

Once the resection has been performed, the fixation pins 74 and the cutting plate 2, 4 can be removed from the humeral head 62. A humeral resection protecting plate can be placed over the resected surface in order to protect the bone from damage during the following surgical steps preparing the glenoid.

A forked retractor can be passed under the scapula in order to lever the humeral head 62 out of the way in order to allow unimpeded access to the glenoid. If the glenoid is not fully visible then a further resection of the humeral head 62 may be required. The forked retractor is placed under the inferior glenoid labrum to move the humerus distally or posteriorly according to the chosen surgical approach (superior-lateral or deltoid-pectoral respectively).

Once the glenoid is fully visible, preparation of the glenoid can begin. Firstly, any remnants of the labrum must be removed from the glenoid face. Additionally, any osteophytes present may also have to be removed to prevent later interference when attaching the mounting plate and the convex bearing surface to the glenoid.

Particular care is needed when determining the attachment point of the mounting plate as this affects the resultant center of rotation of the reverse shoulder prosthesis. The correct mounting plate position achieves optimal glenoid fixation (that is, the mounting plate is fully in contact with the glenoid), good range of motion of the shoulder joint and minimal potential for bone impingement (the humeral component contacting the scapula around the convex bearing head). Ideally, the mounting plate should be positioned on the inferior circular portion of the glenoid. A mounting plate positioning tool may be used to determine the optimal mounting plate position. This comprises a generally circular sizing plate including cut outs such that the glenoid surface is visible through the sizing plate mounted upon a positioning handle which can be manipulated by the surgeon at a point remote from the glenoid. The positioning handle couples to the sizing plate at a point eccentric of the center of the sizing plate such that the center of the plate is visible, and couples to the sizing plate along an axis which diverges from an axis normal to the plate (for instance 20°) in order to allow for maximum visibility of the glenoid.

Once the sizing plate is positioned correctly (for instance, such that its border follows the inferior edge of the glenoid and the sizing plate is parallel to the glenoid face, or with a slight superior tilt) a guide pin is inserted through a guide hole in the center of the sizing plate into the glenoid. The guide pin is inserted either perpendicularly to the glenoid or with a slight superior tilt as determined by the position of the sizing plate. This ensures that an axis defined by the convex bearing head will be either perpendicular to the glenoid or with a slight inferior tilt, thus reducing the risk of scapular notching due to contact between the humeral epiphysis component and the scapula. The position of the guide pin determines the resulting position of the mounting plate as further steps preparing the surface of the glenoid are performed using the guide pin to locate the surgical instruments, as will be described below. The guide pin comprises a 2.5 mm diameter rod and is inserted 3-4 cm into the glenoid using a power tool. The sizing plate and positioning handle may then be removed by sliding over the guide pin.

The mounting plate comprises a circular disc having a slightly convex rear side to be mounted within a corresponding concave depression reamed on the glenoid surface. In order to prepare the glenoid surface a two step reaming process is required. In a first reaming step the glenoid is prepared using a powered circular reamer that is arranged to prepare a reamed portion of bone that is the same size as the mounting plate. As shown in FIG. 10 the powered reamer 100 comprises a circular reaming shell driven by a power tool 102. The reaming shell 100 and the power tool 102 are passed over the guide pin indicated by dashed line 104 by sliding a cannulated shaft over the guide pin such that the reaming position is fixed. The reaming shell 100 may be 27 mm in diameter to ream a concave depression on the glenoid surface corresponding to a typical mounting plate.

Although the mounting plate will be seated correctly after the initial reaming step, the convex bearing head to be mounted upon the mounting plate extends outside of the reamed area. In order to avoid conflict between the convex bearing head and the superior area of the glenoid it is necessary to ream the superior area of the glenoid outside of the first reamed area. As shown in FIGS. 11 and 12, a manually driven reamer 108 is used to ream the superior area 110 of the glenoid 106. The reamer 108 comprises a cannulated shaft 112 which slides over the guide pin indicated by dashed line 104. This ensures alignment of the second reaming step with the first reamed area. The reamer 108 comprises a guide portion 114 which is shaped to be received within the first reamed area. The guide portion 114 has a non-reaming lower surface which is arranged to slidably engage the first reamed portion of the glenoid as the cannulated shaft 112 is rotated about the guide pin. The guide portion 114 includes cut away portions 116 such that its position relative to the first reamed portion of the glenoid 106 can be observed.

Reamer 108 further comprises an eccentric reaming lobe 118 which extends from the guide portion 114 about a portion of the periphery of the guide portion 114. Eccentric reaming lobe 118 has a reaming lower surface positioned to engage the superior area of the glenoid 106. The reaming surface may comprise reaming formations, such as teeth, as is known in the art. By rotating cannulated shaft 112 about the guide pin while applying pressure towards the glenoid 106 the reaming surface of the eccentric reaming lobe 118 is arranged to remove surface portions of the glenoid, until the guide portion 114 is fully seated within the previously reamed portion of the bone. Once this is achieved, as shown in side view in FIG. 12, the glenoid surface is fully prepared to receive the mounting plate and the convex bearing head.

Advantageously, by providing the second reamer as an eccentric reaming lobe, the second reamer is reduced in size compared to a conventional circular reamer such as is used in the first reaming step. This allows the second reamer to be inserted through a smaller incision that would otherwise be the case. For instance, the maximum dimension (that is, the length) of the eccentric reaming lobe 118 may be approximately the same as the diameter of the guide portion 114. The radial extent of the eccentric reaming lobe (from the edge of the guide portion 114 to the edge of the eccentric lobe) may be approximately 8 mm, which is approximately 0.3 times the diameter of the guide portion. Preferably the maximum length and the maximum radial extent from the guide pin of the eccentric reaming lobe is less than the diameter of the guide portion.

As the second reamer is eccentric, it is necessary to manually drive the second reamer such that the eccentric reaming lobe 118 can be rotated back and forth over the superior area of the glenoid in order reduce the impact on the remainder of the glenoid and surrounding tissue. However, if necessary, the second reamer can be used to remove other portions of the glenoid face anteriorly, posteriorly and inferiorly about the circular reamed mounting plate portion.

Optionally, after the second reaming step has been completed, the preparation of the glenoid can be checked by passing a glenoid level checker over the guide pin. The glenoid level checker comprises a disc of the same shape as the mounting plate and an eccentric lobe corresponding to the same amount of bone that is required to be removed from the superior area of the glenoid. The glenoid level checker includes cut outs so that the surface of the glenoid may be viewed while checking the reaming. No space should be visible between the glenoid level checker and the glenoid surface if the reaming has been completed correctly. If space is visible between the glenoid surface and the glenoid level checker then further reaming with either the first and/or the second reamer may be required.

It will be appreciated that in alternative embodiments the eccentric reamer may be varied. For instance, it could be modified to be driven by a motor with a reciprocating action such that the eccentric reaming lobe is repeatedly passed over the same portion of the glenoid surface.

After reaming of the glenoid is complete the guide pin is left in place and used as a drilling guide for drilling a central hole into the glenoid to receive a central pin of the mounting plate. A cannulated stop drill includes a central cavity to receive the guide pin is used. The cannulated stop drill includes a flange ensuring that the central hole is not over drilled.

The mounting plate comprises a disc sized and shaped to be received in the first reamed portion of the glenoid. The mounting plate further includes a central pin corresponding to the central hole drilled in the glenoid. The central pin incorporates a threaded bore for later attachment of the convex bearing head (as will be described in greater detail below). The exterior surface of the central pin is ribbed so as to form a push fit in the central hole. The mounting plate further comprises four fixation holes to receive fixing pins passing into the glenoid to secure the implant. Once the central pin is fully received in the central hole in the glenoid, if necessary the mounting plate may be rotated such that the inferior fixation hole is aligned with the inferior pillar of the glenoid. The surface of the mounting plate further comprises a vertical alignment mark to ensure correct orientation by aligning the vertical alignment mark with the scapular pillar inferiorly and the base of the coracoid process superiorly (that is, the vertical alignment mark is aligned with the long axis of the glenoid). The mounting plate may be gently impacted to ensure that the mounting plate pin is fully seated. Screws may then be implanted through the fixation holes to complete the implantation. The screws may be locking screws, as are known in the art, and may be such that the angle of implantation can be varied to ensure implantation into good bone stock. Alternative, any other suitable form of screw may be used. The mounting plate implantation is then secure and further humeral head preparation can be carried out.

To ream the resected humeral head so as to create a cavity to receive the epiphysis component of the humeral implant, it is necessary to insert an intramedullary reaming guide into the cavity in the reamed medullary canal. Referring to FIG. 13, the intramedullary reaming guide 200 comprises an elongate stem portion 202 which defines a longitudinal axis, and a neck portion 204, which defines a neck axis inclined to the longitudinal axis. The intramedullary reaming guide 200 is provided in a range of sizes determined by the diameter of the stem portion 202. The size of intramedullary reaming guide chosen is determined by the diameter of the intramedullary cavity reamed into the humeral head 62, as described above. The intramedullary cavity defines a longitudinal axis, which is parallel to or aligned with the longitudinal axis of the humerus. Consequently, when the intramedullary reaming guide 200 is inserted into the intramedullary cavity, rotating the stem portion 202 rotates the neck portion 204 about the longitudinal axis of the humerus.

The neck portion 204 further comprises a flange 206, such that when the intramedullary reaming guide 200 is fully inserted into the intramedullary cavity, further insertion is prevented by the flange 206. Adjacent to the flange 206 is a reference formation 208, comprising a rib. The reference formation 208 serves to ensure that any posterior offset when reaming the epiphysis cavity is precisely orientated relative to the neck portion 204, as will be described in greater detail below. The reference formation 208 also allows the intramedullary reaming guide to be coupled to an alignment instrument, as will be described below.

The stem portion 202 further comprises at least one and preferably two ribs 210 arranged to cut into the cancellous bone around the intramedullary cavity as the intramedullary reaming guide 200 is driven into the intramedullary cavity. The ribs 210 prevent the fully inserted intramedullary reaming guide from being rotated about the axis of the stem once the intramedullary reaming guide 200 is fully inserted. Therefore, it is essential that the intramedullary reaming guide 200 is correctly orientated before being driven into the humerus.

As noted above, the neck portion 204 defines the reaming axis for reaming the humeral head 62 in order to create a cavity for the epiphysis portion of the humeral component. It is important to ensure the epiphysis cavity is correctly reamed, such that once implanted the rim of the epiphysis portion is exactly parallel to the resection surface. The rim of the epiphysis portion may be required to be congruent with the resection surface. Normally, this requires that the axis of the neck portion 204 is perpendicular to the resection surface, however the axis of the neck portion 204 may lie anywhere within a plane defined by the axis of the cavity and a line extending from the axis of the cavity perpendicular to the resection surface. To ensure that the axis of the neck portion 204 lies within this plane, the intramedullary reaming guide 200 must be correctly orientated before being driven into the bone and locked in position by the ribs 210.

In order correctly orientate the intramedullary reaming guide 200 an alignment instrument 212 is provided as illustrated in FIG. 13. Alignment instrument 212 comprises a handle 214 and coupler 216 for coupling to the intramedullary reaming guide 200. The coupler 216 comprises a clamp arranged to engage rib 208 on the intramedullary reaming guide 200. Neck portion 204 is passed through coupler 216 until flange 206 comes to rest against the coupler 216. The clamp may then be tightened onto rib 208 by turning knob 218, which is coupled to internal rod 220 which in turn couples to the clamp. Knob 218 is turned until internal rod 220 is no longer visible. Knob 218 further comprises an impaction surface 218A. Once the intramedullary reaming guide 200 is fully received in alignment instrument 212, the longitudinal axis of handle 214 is aligned with the longitudinal axis of the stem component 202 while the stem portion 202 is partially received in the intramedullary cavity. Once correctly aligned, an impaction force can be applied to impaction surface 218A drives the intramedullary reaming guide 200 fully into the cavity.

The alignment instrument 212 further comprises a plane finder 222. Plane finder 222 comprises a plate having a surface which defines a plane forming an angle with respect to the longitudinal axis of the handle 214 which is the same as that at which the resection surface intersects the longitudinal axis of the humerus. Typically, this is 155°. If the neck portion 204 is arranged to be perpendicular to the resection surface, then this is the same angle at which the axis of the neck portion 204 intersects the axis of the stem portion 202 of the intramedullary reaming guide 200.

Referring now to FIG. 14, this illustrates the intramedullary reaming guide 200 coupled to the alignment instrument 212. As can be seen, the plane finder 212 is slidably mounted with respect to the handle 214 such that it can be raised and lowered parallel to the longitudinal axis of handle 214. The plane finder 222 is formed as a horse shoe such that it can slide over the intramedullary reaming guide 200. The plane finder 222 is further provided with parallel support bars 224, 226 which are arranged to be parallel to the longitudinal axis of the handle. Support bars 224, 226 are slidably received in holes passing through coupler 216, which comprises a mounting bracket. Cross bar 228 prevents the plane finder 222 from being fully removed from the alignment instrument 212.

Figures 15, 16, 17:
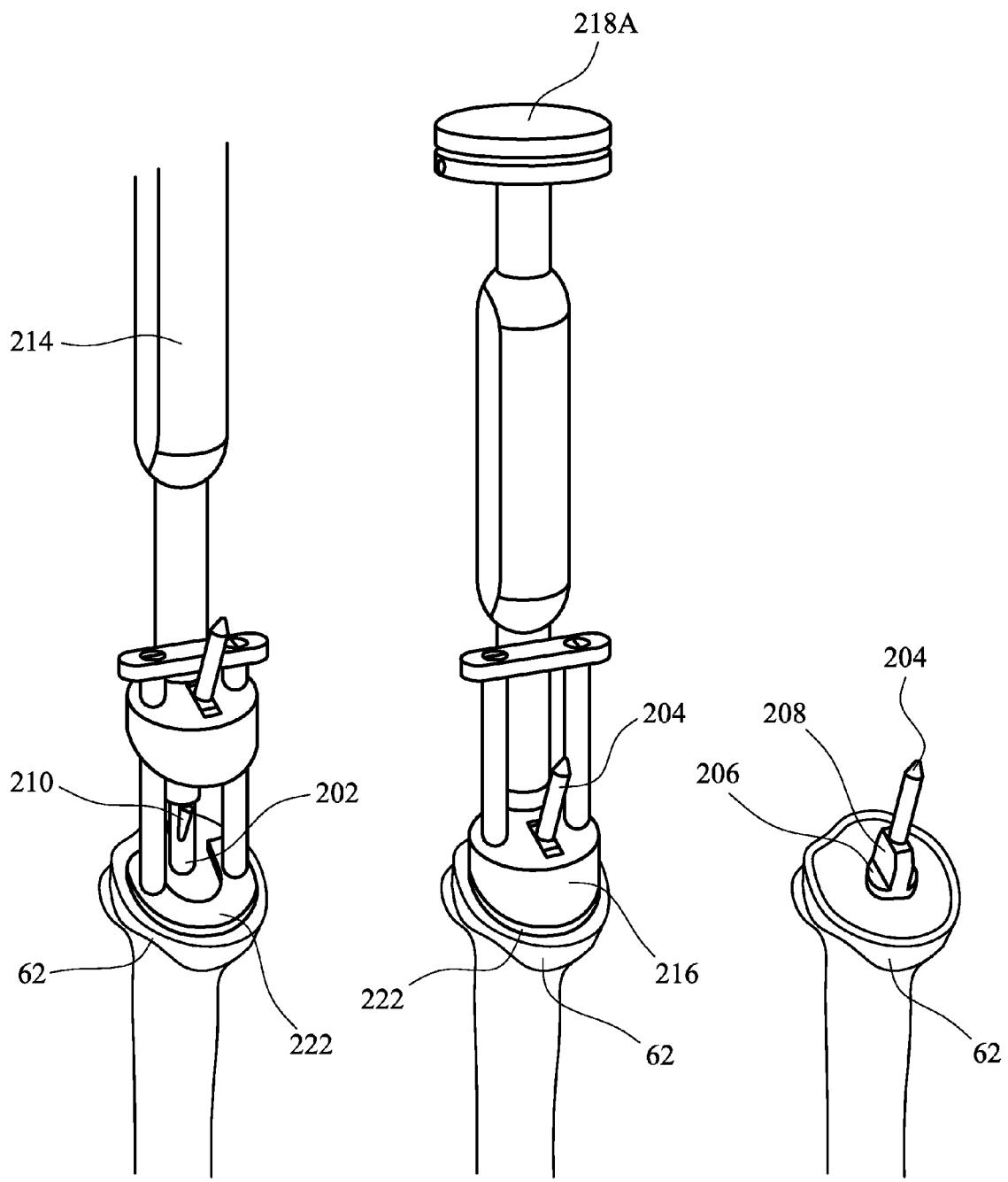
FIGS. 15 and 16 illustrate the intramedullary reaming guide and the alignment instrument of FIG. 13 during implantation of the intramedullary reaming guide into a cavity reamed in the medullary canal of the humerus.
FIG. 17 illustrates the intramedullary reaming guide of FIG. 13 implanted into a cavity reamed in the medullary canal of the humerus.

The process of inserting the intramedullary reaming guide 200 into the intramedullary cavity begins with sliding plane finder 222 parallel to the axis of handle 214 until it is fully extended over the intramedullary reaming guide 200. The stem portion 202 can then be progressively inserted into the intramedullary cavity until the plane finder 222 contacts the resection surface. The handle 214 (and thus the plane finder 222 and the intramedullary reaming guide 200) can then be rotated about the longitudinal bone axis until the plane defined by the surface of the plane finder 222 is parallel to the resection surface, as shown in FIG. 15. As can be seen in FIG. 15, the ribs 210 have not yet made contact with the cancellous bone of the humeral head 62 and so the alignment instrument 212 together with the intramedullary reaming guide 200 can freely rotate and slide within the intramedullary cavity. Once correctly positioned, the intramedullary reaming guide 200 can be driven home by applying an impaction force to impaction surface 218A until the plane finder is brought up against mounting bracket 216 as shown in FIG. 16. At this point, ribs 210 engage the cancellous bone surrounding the intramedullary cavity and prevent further rotation of the intramedullary reaming guide 200.

The flange 206 of intramedullary reaming guide 200 is received within a recess on the underside of mounting bracket 216, and the plane finder 222 is similar received within a peripheral recess around the underside of mounting bracket 216, such that when the plane finder 222 is in contact with both the resection surface and the mounting bracket 216 the intramedullary reaming guide 200 is fully inserted into the intramedullary cavity. The underside of flange 206 is in contact with the resection surface. The alignment instrument 214 can then be decoupled from the intramedullary reaming guide 200 by unscrewing knob 218 leaving the intramedullary reaming guide 200 in position with neck portion 204 protruding from the resection surface of the humeral head 62 as shown in FIG. 17.

As will be appreciated, the alignment of the neck portion 204 is directly related to the alignment of the support rod about the axis of the cavity during the initial resection step described above. That is, after the initial rotational alignment of the cutting guide assembly relative to the patient's forearm, each surgical step performed upon the humeral head 62 is intended to preserve that original orientation.

It will be appreciated that in alternative embodiments the plane finder may differ. For instance it need not be formed as a horse shoe, and may instead be any other shape such as an elongate bar. The only limitation to the shape of the plane finder is that it must be arranged to move relative to the longitudinal axis of the alignment instrument and arranged to contact the resection surface, such that rotation of the alignment instrument causes the plane finder to rotate until it is parallel to the plane of the resection surface.

After the intramedullary reaming guide 200 has been implanted, the humeral head is ready for reaming to create a cavity for the epiphysis component. As discussed above, the humeral component may either be a single integral implant incorporating both the stem component and the humeral component, or it may be modular in which different size stem components and epiphysis components can be coupled together. Advantageously this allows the epiphysis component to be offset from the position of the neck portion 204 of the intramedullary reaming guide 200 in a posterior direction, which can increase joint mobility. Furthermore, in order to achieve a more secure implantation, it is preferable to insert the stem component in an anatomic orientation referenced to the bicipetal groove (as discussed in greater detail below). However, the orientation of the epiphysis component may differ from the anatomic position according to the orientation chosen by the surgeon when resecting the humeral head, as discussed above. Consequently, the modular humeral implant allows for this variation (i.e., distal offset) between the stem component and the epiphysis component.

As will now be described, an instrument kit for reaming an epiphysis cavity allows for an optional posterior offset of the epiphysis component. Additionally, the diameter of the reamed epiphysis cavity may be varied. Advantageously, the center of the reamed epiphysis cavity and the size of the reamed epiphysis cavity may be chosen in order to ensure the best possible coverage of the resection surface (that is, the largest epiphysis cavity). FIG. 18 illustrates the resected humeral head 62 with the neck portion 204 extending perpendicularly from resection surface (only the tip of neck portion 204, flange 206 and reference formation 208 are visible). Positioned over the neck portion 204 is a centered adapter sleeve 300 which is arranged to ensure that reaming for the epiphysis cavity is centered about the neck portion 204 of the intramedullary reaming guide 200. The centered adapter sleeve 300 comprises a generally cylindrical component, the outer surface of which comprises a reaming guide such that a reaming head having a cylindrical bore can be positioned over the adapter sleeve 300, thereby ensuring that the reaming head is correctly aligned with the humeral head 62.

Adapter sleeve 300 further comprises a bore 302 corresponding to and configured to accept the diameter of the neck portion 204. The bore 302 extends to a proximal part of the adapter sleeve 300 such that the tip of the neck portion 204 is visible, thus confirming that the adapter sleeve 300 is fully seated on the intramedullary reaming guide 200. At a distal end of adapter sleeve 300 is a collar 304, comprising a groove shaped to accept the reference formation 208. Consequently, when the adapter sleeve 300 is fully seated on neck portion 204 it is prevented from rotating about the neck portion 204.

The adapter sleeve 300 shown in FIG. 18 is a centered adapter sleeve, that is the bore 302 is coincident with the outer surface of the adapter sleeve 300, and thus is suitable for reaming where no posterior offset of the epiphysis cavity is required. As will be described below, adapter sleeves 300 with varying degrees of posterior offset (that is, non-coaxial bores 302) may be used to achieve a posterior offset of the epiphysis component.

In addition to allowing for variable posterior offset, the instrument kit further allows for different diameter epiphysis cavities to be reamed using reamers with different size reaming heads. However, before reaming begins, reaming sizing guides can be used to determine the correct size of reaming head. Referring to FIGS. 19 and 20, these respectively show the same centered adapter sleeve 300 illustrated in FIG. 18 in combination with first and second sizing guides 306, 308. The sizing guides 306, 308 comprise a sleeve 310, 312 arranged to fit over the outside of the centered reaming adapter 300 and a disc 314, 316. Discs 314, 316 come to rest against the resection surface so that the surgeon may view what the diameter of the reamed epiphysis would be if a reamer having a reaming head of the same size as the sizing guide disc is used. Discs 314, 316 include cut outs so that the resection surface can be viewed through, as well as around, the disc. The sizing guide 308 shown in FIG. 19 is a smaller, size 1, guide, and the sizing guide shown 308 in FIG. 20 is a larger size 2 guide. The disc 314 of the size 1 guide 306 may be approximately 38 mm in diameter and the disc 316 of the size 2 guide may be approximately 42 mm in diameter. The bore of each sizing guide 306, 308 fitting over the adapter sleeve 300 is the same, thus allowing the adapter sleeves 300 and sizing guides 306, 308 to be interchanged. The sizing guides 306 may be color coded so that they can be matched to the same color (and same size) reaming head when reaming is conducted.

As can be seen in FIGS. 19 and 20, both sizing guide 306, 308 extend outside of the resection surface anteriorly. Consequently, it is apparent that the centered adapter sleeve 300 is not appropriate for this particular humeral head 62. By providing a posterior offset using a posteriorly eccentric adapter sleeve, improved coverage of the resection surface can be obtained, as will now be described.

Figures 21, 22, 23:
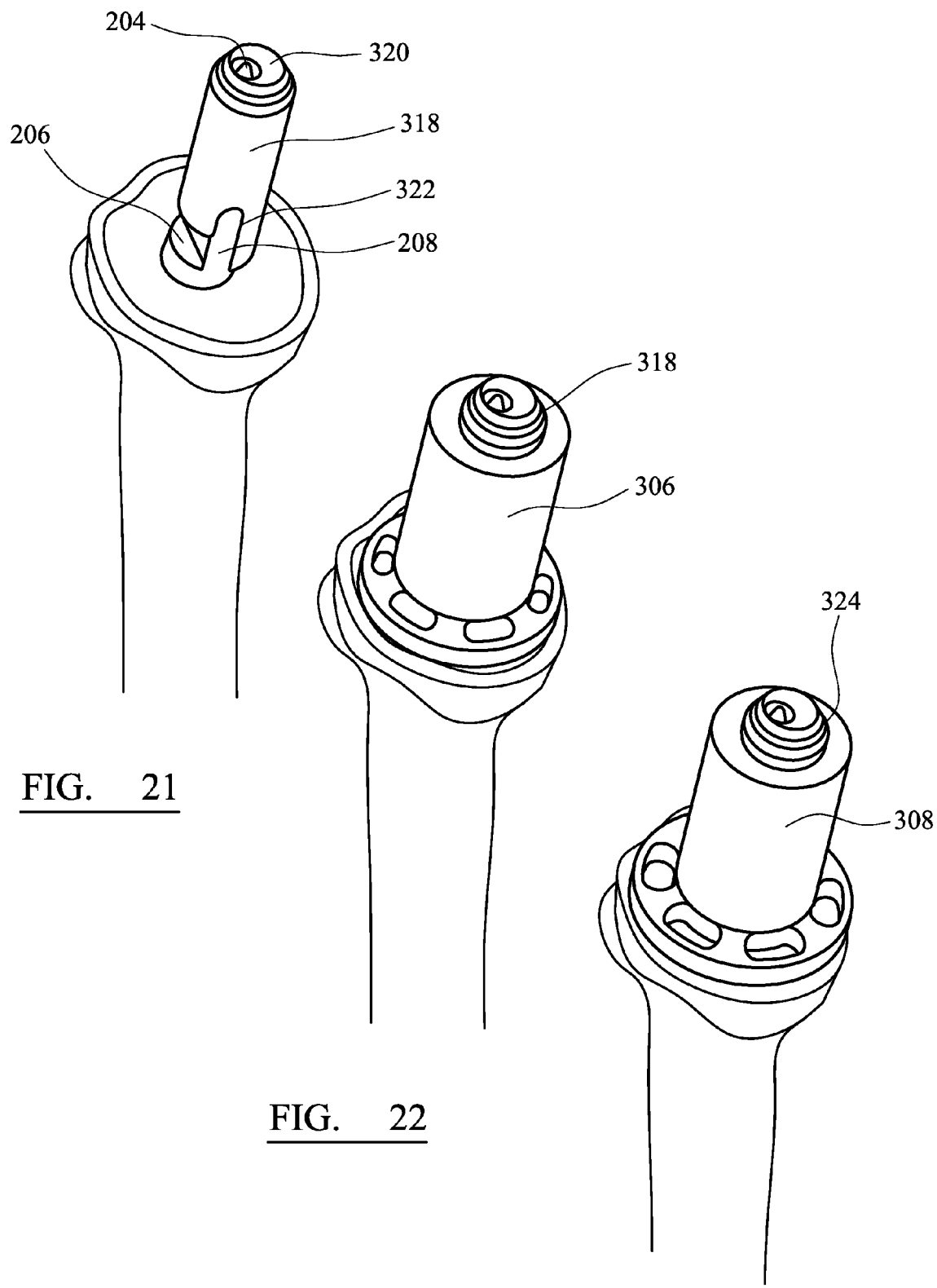
FIG. 21 illustrates a first eccentric reaming adapter coupled to a intramedullary reaming guide implanted into a cavity reamed in the medullary canal of the humerus as illustrated in FIG. 17.
FIG. 22 illustrates a first sizing guide coupled to the eccentric reaming adapter illustrated in FIG. 21.
FIG. 23 illustrates a second sizing guide coupled to a second eccentric reaming adapter illustrated, which in turn is coupled to a intramedullary reaming guide implanted into a cavity reamed in the medullary canal of the humerus as illustrated in FIG. 17.

Referring now to FIG. 21, the centered adapter sleeve 300 shown in FIGS. 19 and 20 has been replaced by a new adapter sleeve 318 which presents a posterior offset. The offset adapter sleeve 318 presents generally the same outer cylindrical shape such that it can receive the same sizing guides 306, 308 shown in FIGS. 19 and 20. However, for offset adapter sleeve 318, the bore 320 which receives neck portion 204 is offset from the axis of the adapter sleeve defined by the outer cylindrical surface. Markings on the outside of the offset adapter sleeve 318 ensure that the offset is positioned in a posterior direction as shown in FIG. 21 (which illustrates the arrangement for a right humerus).

As with the centered adapter sleeve 300 shown in FIG. 18, the bore 320 extends to a proximal part of the reaming adapter 318 such that the tip of the neck portion 204 is visible, thus confirming that the adapter sleeve 300 is fully seated on the intramedullary reaming guide 200. At a distal end of adapter sleeve 318 is a collar 322, comprising a groove shaped to accept the reference formation 208. Consequently, when the adapter sleeve 300 is fully seated on neck portion 204 it is prevented from rotating about the neck portion 204. As will be apparent, the groove 322 for offset adapter sleeve 318 is exactly the same as for centered adapter sleeve 300 and in the same relationship with bore 320 in order to ensure a correct fit over neck portion 204. However, the groove 322 is offset from the central axis of the offset adapter sleeve 318 such that the groove is defined by two fingers of differing thicknesses.

As noted above, both centered adapter sleeve 300 and offset adapter sleeve 318 are generally cylindrical and have the same exterior diameter to ensure compatibility with the sizing guides 306, 308. The exterior diameter of the adapter sleeves 300, 318 is larger than the diameter of flange 206 to ensure that even for the offset adapter sleeve 318 the exterior surface of each adapter sleeve extends further outwards than the flange 206 and the reference formation 208 in all radial directions about the neck portion 204. This ensures that when a reaming head is passed over the adapter sleeves 300, 318 (or any other adapter sleeve with a different degree of posterior offset), there is no contact between the reaming head and the intramedullary reaming guide.

Referring to FIG. 22, the smaller size 1 sizing guide 306 is positioned over offset adapter sleeve 318 to check for coverage of the resection surface. Offset reaming guide 318 is color coded the same color as the size 1 sizing guide 306. Six different epiphyses are available for the final implant: first and second size centered epiphyses (corresponding to the size 1 and size 2 sizing guides shown in FIGS. 19 and 20), an epiphysis with a first degree of offset having the diameter of the size 1 sizing guide shown in FIG. 22 (in left and right shoulder options) and an epiphysis with a second, larger, degree of offset having the diameter of the size 2 sizing guide shown in FIG. 23 discussed below (also in left and right shoulder options). Each offset epiphysis has left and right options, which are mirror images of one another.

While a reamer matched to the size of the larger sizing guide could be used on the adapter sleeve shown in FIGS. 21 and 22, this would not match a final implant epiphysis. Consequently, while either size sizing guide may be used in conjunction with the centered adapter sleeve, the correctly color matched sizing guide must be used with each offset adapter sleeve. If the bone coverage is not sufficient then a new adapter sleeve 324 with an increased posterior offset as shown in FIG. 23 can be used in combination with the size 2 sizing guide 308. Increased offset adapter sleeve 324 is color coded the same color as the size 2 sizing guide 308.

In alternative embodiments of the present invention there may be any number of adapter sleeves with differing degrees of offset. Similarly, there may be any number of sizing guides, which may be used with any adapter sleeve (offset or centered). However, it will be appreciated that such flexibility would necessarily be at the expense of having to provide a larger number of different sized and shaped epiphyses for the final implant to account for all possible combinations of size of offset and size of reaming head (corresponding to the sizing guide).

The color (and hence size) of the chosen sizing guide 306, 308 must be matched to the same color reaming head. Careful note must be taken of whether a centered or which posterior offset adapter sleeve is used, and the size of the reaming head used as this determines which epiphysis component to use during final implantation of the humeral component.

Figure 24:
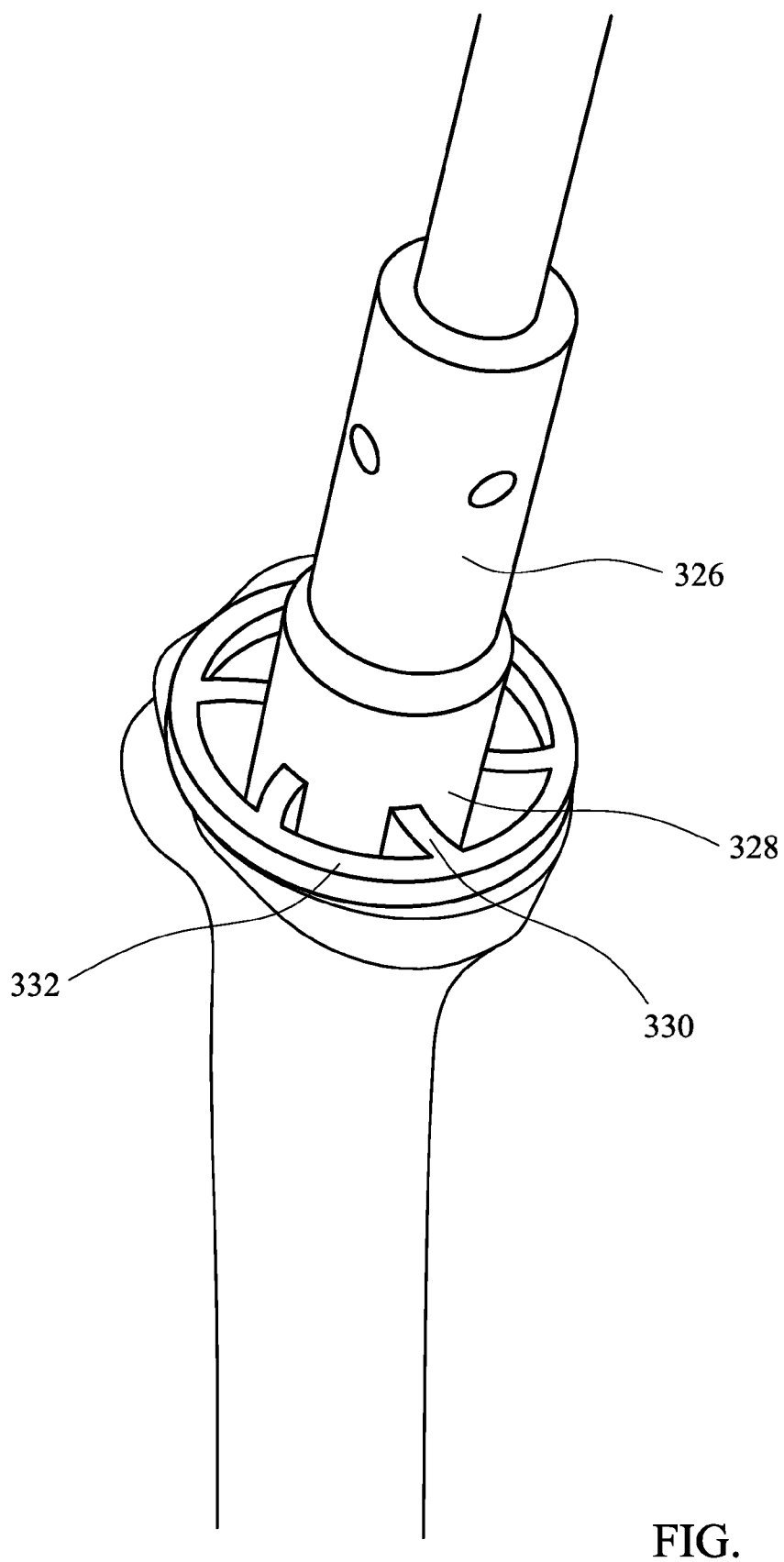
FIG. 24 illustrates a reaming head being used to ream an epiphysis cavity in a resected humeral head.

Once the optimal adapter sleeve and sizing guide have been selected the sizing guide is removed and the matching reaming head 326 is passed over the adapter sleeve such that powered reaming of the epiphysis cavity can begin as shown in FIG. 24. Reaming head 326 comprises a reaming shell 328 including spaced apart reaming formations 330 and an exterior smooth reamer flange 332. Reaming is complete when the exterior reamer flange 332 is fully in contact with the resection surface around the whole of the reamer shell 328.

Once reaming of the humeral head 62 is complete the reaming head 326 and the adapter sleeve can be removed from neck portion 204. The intramedullary reaming guide 200 can then be extracted from the intramedullary cavity by connecting the intramedullary reaming guide 200 to the alignment instrument 212 shown in FIG. 13 and pulling axially out of the intramedullary cavity. If any cancellous bone remains unreamed within the epiphysis cavity around the previous position of the intramedullary reaming guide 200 then this can be manually removed.

After reaming of the epiphysis cavity is complete, the intramedullary cavity must be enlarged in order to accommodate the stem portion of the humeral component. As described above, the intramedullary cavity is initially formed as a continuous diameter reamed bore. At a distal portion, the stem portion comprises a corresponding diameter shaft (a range of diameter stem portions being available corresponding to the largest size reamer used to create the intramedullary cavity). However, proximally, the stem portion comprises anterior and posterior ribs and, optionally, a pronounced medial rib, all of which serve to prevent rotation within the intramedullary cavity and also to increase the engagement of the stem portion with cancellous bone. Therefore, the intramedullary cavity must be enlarged in these areas.

As discussed above, the resection surface, and hence the position of the epiphysis component, can be orientated about the longitudinal axis of the bone defined by the intramedullary cavity in order to provide a desired degree of retroversion or anteversion to the reverse shoulder prosthesis. Consequently, the resection surface may be rotationally offset from the anatomical position (that is, the rotational position of the natural humerus neck axis about the longitudinal axis of the humerus). However, it is advantageous to insert the stem portion in an anatomical position in order to increase the strength of the joint. Additionally, this provides the maximum amount of cancellous bone for the stem portion to engage. Therefore, it is necessary to measure the rotational offset between the rotational position of the stem portion cavity (that is, the anatomical position of the natural humerus if the stem portion is exactly aligned with the anatomical position) and a line extending normal to the resection surface and intersecting the longitudinal axis of the intramedullary cavity. This measurement may either be performed at the same time as enlarging the intramedullary cavity or as a separate processing step. The measured rotational offset may then be used during assembly of the humeral component to rotationally offset the stem portion and the epiphysis portion. It is important to correctly measure this offset in order to ensure that the rim of the epiphysis portion is parallel to the resection surface. Typically, the rim of the epiphysis component is required to be congruent with the resection surface.

Figure 25:
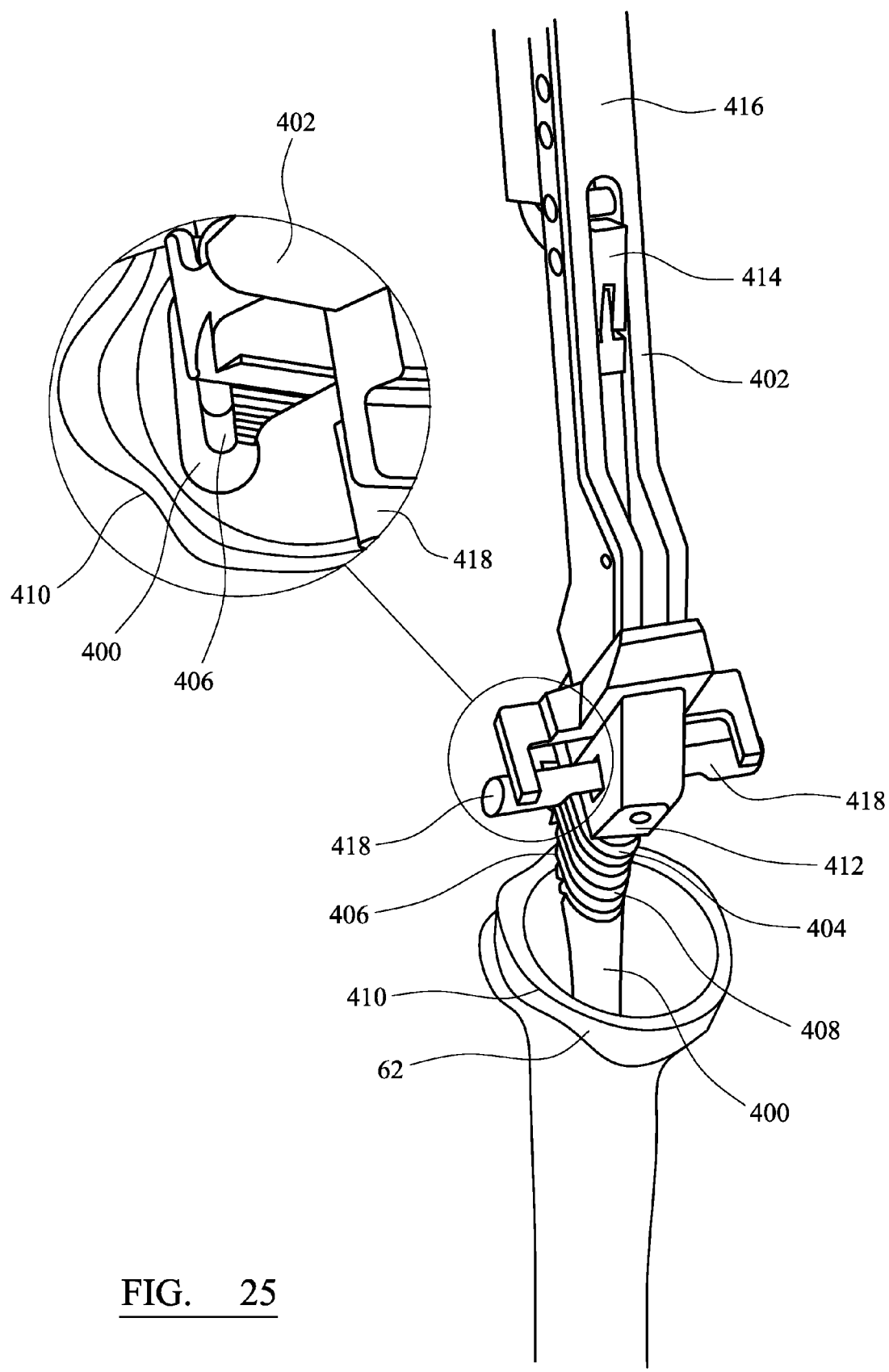
FIG. 25 illustrates a broach and a broach insertion instrument being used to enlarge a reamed cavity within the medullary canal of a resected humeral head.

Referring now to FIG. 25, this illustrates a broach 400 and a broach insertion instrument 402. The broach insertion instrument 402 incorporates means for measuring the rotational offset. The broach 400 comprises at a distal portion a smooth shaft of a corresponding diameter to that of the intramedullary cavity reamed before. FIG. 25 illustrates the broach 400 partially inserted into the humeral head 62. At a proximal end the broach 400 comprises cutting teeth 404 adapted to engage and cut into cancellous bone as the broach 400 is driven into the humeral head 62. Cutting teeth 404 form an anterior cutting fin 406, a medial cutting fin 408 and a posterior cutting fin (not visible in FIG. 25).

The enlarged portion of FIG. 25 illustrates from a superior angle the anterior cutting fin 406. To ensure that the broach 400 (and hence, the implanted stem portion) are in the anatomic position, the anterior cutting fin 406 should be aligned with the anterior aspect of the bicipital groove 410.

The broach insertion instrument 402 includes an engagement mechanism 412 for engaging the distal end of broach 400 that may comprise a clamp which is engaged by manipulating lever 414. The instrument 402 also comprises a handle portion 416, which terminates at an impaction surface (not shown in FIG. 25) to which an impaction force may be applied to drive the broach 400 into the intramedullary cavity.

The instrument further comprises a depth stop 418, which comprises a rocker bar extending through a portion of the instrument proximal to the broach engagement mechanism 412. The rocker bar 418 pivots within the instrument 402 and extends from the instrument 402 on the anterior and posterior sides. The rocker bar comprises a plane finder. As broach 400 is driven into the intramedullary cavity the rocker bar contacts the resection surface at the cortical shell of the humeral head 62 and aligns itself with the plane of the resection surface. In the event that the resection surface is oriented in the anatomical position (that is, there is no rotational offset) both arms of the rocker bar 418 will contact the resection surface at the same time. However, if the resection surface is retroverted or anteverted one or the other arm of the rocker bar 418 will contact the resection surface first, causing the rocker bar to pivot about its mid point. Insertion of the broach 400 into the intramedullary cavity continues until both arms are in contact with the resection surface. The rocker bar 418 therefore ensures the correct extent of insertion of the broach 400 into the intramedullary cavity, and therefore ensures the cavity is correctly sized to receive the stem portion. Increased rotational offset results in an increased pivot angle of the rocker bar 418 relative to the broach insertion instrument 402.

Figure 26:
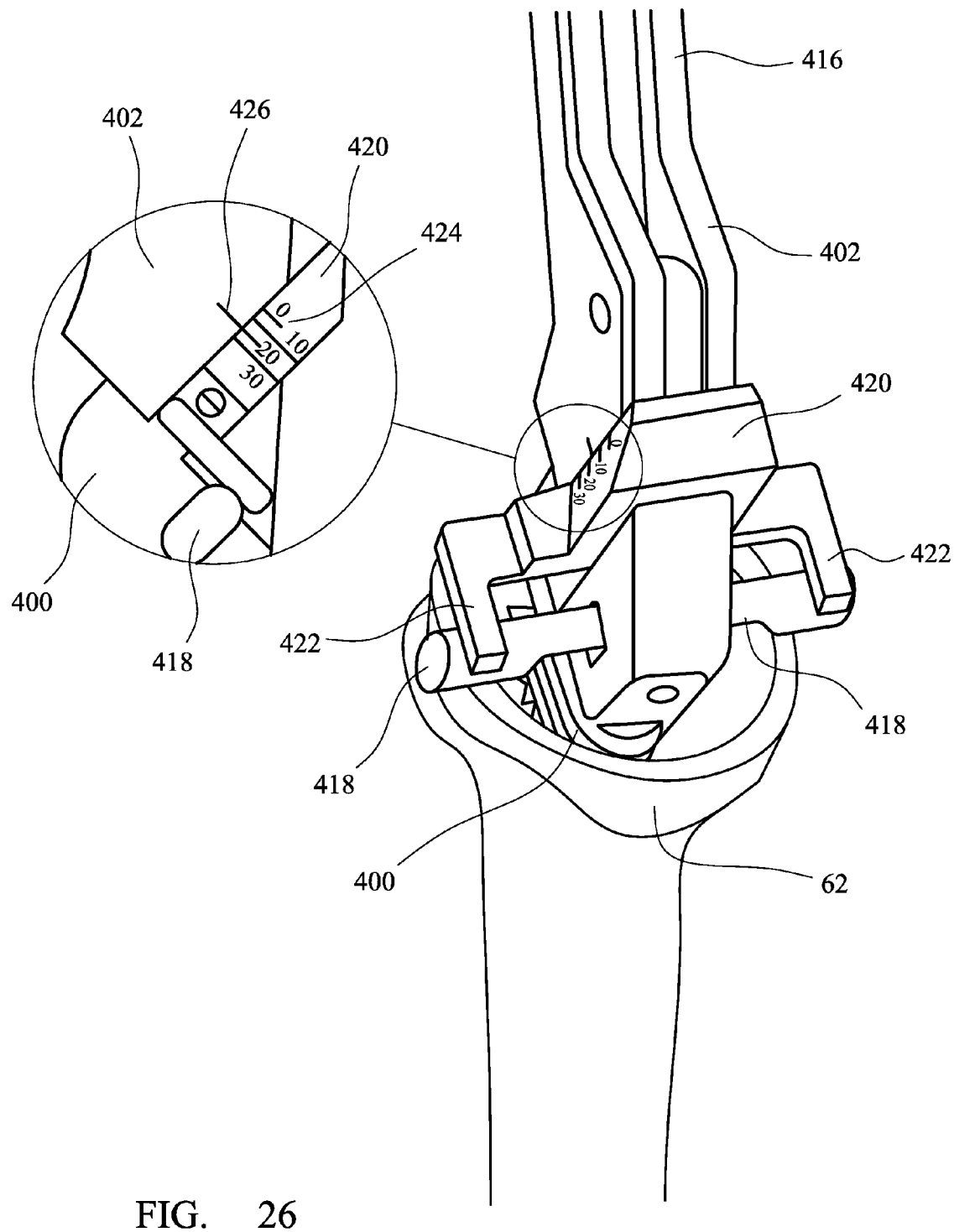
FIG. 26 illustrates portions of the broach and broach insertion instrument of FIG. 25 being used to measure a rotational offset between the rotational position of the broach and a line which extends normal to a resection surface and intersects a longitudinal axis of the humerus defined by the reamed cavity.

Referring to FIG. 26, this illustrates the broach insertion instrument 402 once the broach 400 has been fully inserted into the intramedullary cavity. As can be seen, both arms of rocker bar 418 are in contact with the resection surface. The rocker bar 418 is pivoted with respect to the instrument handle 416 due to the resection surface being retroverted relative to the anatomical position of the broach 400. The instrument 402 further comprises a yoke 420 which is slidably mounted on the instrument 402 such that it can slide in the plane in which the rocking bar 418 pivots. Yoke 420 comprises legs 422 that are configured to contact the rocking bar 418. When the rocking bar 418 pivots, it causes the yoke 420 to rise up away from the rocker bar 418. It will be appreciated that the plane in which yoke 420 slides may differ from the pivot plane of rocker bar 418 and that the yoke 420 will still move so long as its plane is not perpendicular to the rocker bar pivot plane.

If there is no rotational offset (zero retroversion) both legs 422 will be in contact with the rocker bar 418 and the yoke will not rise up from its rest position. However, once the rocker bar 418 begins to pivot, only one leg 422 will be in contact with the rocker bar 418. Yoke 420 slides within parallel grooves formed in the sides of insertion instrument 402. The yoke 420 is constrained by these grooves such that it cannot pivot, the degree to which the yoke 420 rises up is the same regardless of which arm of rocking bar 418 is rising up.

It will be appreciated that an increased rotational offset will cause the rocker bar 418 to pivot by an increased amount. The direction in which rocker bar 418 pivots (that is, which arm is uppermost) is dependent upon whether the resection surface is retroverted or anteverted. The amount by which yoke 420 rises up when rocker bar 418 pivots it directly proportional to the magnitude of the of the rocker bar pivot, and hence is indicative of the rotational offset between the stem portion and the epiphysis portion. The enlarged portion of FIG. 26 illustrates a scale 424 applied to either side of the yoke 420. Scale 424 is read at a reference mark 426 on the body of the broach insertion tool. When there is no rotational offset (rocker bar 418 is level and the yoke 420 is at its lowest position) the reference mark 426 indicates 0° retroversion. Scale 424 is calibrated to directly indicate the rotational offset. Therefore, if the resection surface is not in the anatomical position reading scale 424 will indicate the degree of rotational offset (in FIG. 26 the scale 424 indicates up to a 30° rotational offset). Whether the rotational offset is in respect of retroversion or anteversion is determined by noting which arm is uppermost (and in contact with yoke 420). If the anterior arm of rocker bar 418 is uppermost, the resection surface is retroverted and if the posterior arm is uppermost, the resection surface is anteverted.

It will be appreciated that in alternative embodiments of the present invention the broach insertion instrument may comprise alternative means for measuring movement of the yoke (or other plane finder component) such as electronic detection means.

As will be appreciated, it is advantageous for the rocker bar 418 to be as long as possible, and for the yoke legs 422 to contact the rocker bar 418 as far apart as possible as this amplifies the degree to which the yoke 420 rises up for a given rotational offset. Typically, the rocker bar is 54 mm, though it will be appreciated that the length of the rocker bar must be greater than the diameter of the cavity reamed in the resection surface of the epiphysis. The proximal place of the implanted epiphysis has a diameter which typically ranges between 38 mm and 41 mm according to the required size of the implant. Therefore, the rocker bar may vary between 40 mm and 70 mm. The yoke legs 422 are arranged to contact the rocker bar 418 towards either end of the rocker bar 418, for instance spaced apart by between 40 mm and 70 mm.

It will be appreciated that other mechanisms for measuring the rotational offset could be provided. The rocker bar 418 constitutes a plane finder adapted to alter its position relative to the broach insertion tool to conform to the plane of the resection surface. Specifically, the movement is a pivot motion about an axis which is perpendicular to the axis of the broach insertion instrument handle 416. The movement relative to the handle 416 could take other forms. For instance, the plane finder may be formed as a plate having a plane which intersects the axis of the handle 416 at the same angle as that at which the resection surface intersects the longitudinal axis of the intramedullary canal. The plane finder may be arranged to be rotatable about the handle 416 such that as the broach 400 is driven into the bone the plane finder slides round until its plane is congruent with the resection surface. The rotation of the plane finder about the handle 416 may then be measured and is equivalent to the rotational offset. As noted above, the reaming and measurement steps may be separated such that a separate measurement tool could be used have a first component for insertion into the intramedullary cavity and a plane finder as discussed above.

Figure 27:
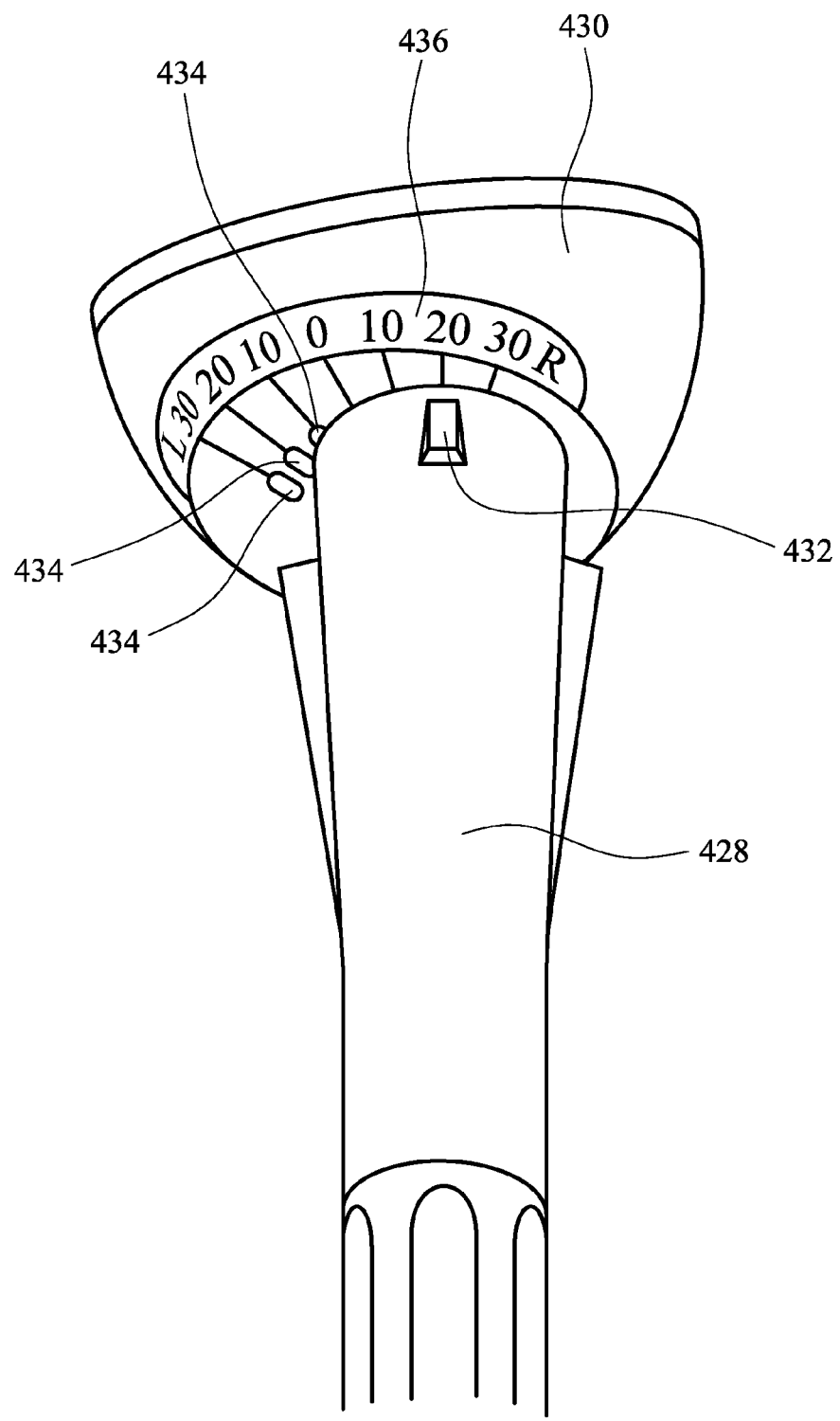
FIG. 27 illustrates part of a modular humeral component of a reverse shoulder prosthesis.

Referring now to FIG. 27, this illustrates the humeral component for insertion into the reamed humeral head 62. Alternatively, the component illustrated in FIG. 27 may be a trial component for insertion and testing prior to insertion of the final component. FIG. 27 illustrates a proximal part of the stem portion 428 and the epiphysis portion 430. The stem portion 428 further comprises a reference formation 432 and the underside of the epiphysis 430 comprises a series of notches 434 and a scale 436. An upper surface of the stem 428 further comprises a single protrusion (not visible in FIG. 27) arranged to engage one of notches 434. The measured rotational offset of the enlarged intramedullary cavity and the epiphysis cavity (measured using the yoke system of the broach insertion instrument 402 of FIGS. 25 and 26) according to whether the offset is retroverted or anteverted, is used to select the appropriate notch 434 into which to engage the stem protrusion, as selected by aligning reference formation 432 with the required position on scale 436. A locking screw (not visible in FIG. 27) passes through the epiphysis portion into the stem portion, thereby locking the humeral component and preserving the selected degree of retroversion or anteversion such that the humeral component conforms to the shape of the cavity reamed in the humeral head 62. The stem portion 428 is selected according to the diameter of the reamed intramedullary cavity. The epiphysis portion 430 is selected from an available range according to whether the reamed epiphysis cavity was centered or posteriorly offset, and according to the size of the epiphysis reaming head used.

Once assembled, the humeral implant can be manipulated using a humeral component driver which comprises means for releasably engaging the inside part of the epiphysis component. This allows the humeral component to be inserted into the intramedullary cavity without contacting the exterior surface of the implant (thereby preserving the hydroxyapetite coating which serves to encourage bone in growth securing the implant in position). The humeral component driver incorporates alignment holes to receive an alignment pin similar to the alignment pin shown in FIG. 3 allowing the alignment of the humeral component to be referenced to the patient's forearm, thereby ensuring that the humeral component is aligned with the resection surface. Furthermore, during insertion of the humeral component, the anterior rib of the stem component is aligned with the anterior aspect of the bicipetal groove similar to the alignment of the broach shown in FIG. 25.

As noted above, in place of the modular humeral component an integral humeral implant comprising both a stem and an epiphysis may be used. The integral humeral component is particularly suited to applications in which the humeral component is secured using bone cement. The surgical steps for preparing the intramedullary cavity to receive the integral implant are generally the same as described above for the modular implant. However, it is not possible to provide a posterior offset for the epiphysis. Consequently, only a single, centered reaming adapter is provided for reaming the epiphysis cavity, although a choice of size of reaming head is available and reaming sizing guides may be used to determine the reaming head to be used, as described above. It is not necessary to enlarge the intramedullary cavity using a broach to receive an integral component as fixation is achieved using bone cement and therefore the humeral component stem does not incorporate fins. During insertion of the humeral component into the intramedullary cavity rotational alignment of the component and the resection surface is achieved by using an alignment pin orientated to be parallel to the patient's forearm axis, as described above for the modular humeral implant.

Once the humeral implant is in position, the convex bearing head can be attached to the mounting plate. As with the humeral component, a trial convex bearing head may first be attached so that the optimal positioning and size of the convex bearing head can be determined. The convex bearing head comprises a convex dome including a recessed cavity on the reverse side corresponding to the size and shape of the mounting plate. As is shown generally in FIG. 30 and described in more detail below, a hole passes through a central portion of the convex bearing head such that the convex bearing head can be secured to the mounting plate by passing a screw into a threaded socket extending into the central pin of the mounting plate. At its broadest point the convex bearing head is preferably either approximately 38 mm or 42 mm in diameter according to the chosen size, but the size may range from 35 mm to 45 mm. Additionally, the convex bearing head may be circular or eccentric about the screw hole. The convex bearing head preferably overlaps the glenoid inferior limit by about 3 mm to 5 mm. The overlap reduces contact between the humeral epiphysis and the scapular pillar during rotation of the shoulder.

When securing the convex bearing head to the mounting plate a 1.5 mm diameter guide pin may be inserted into the central hole in the mounting plate in order to ensure correct alignment of the convex bearing head. A fixation hole within the convex bearing head is passed over the guide pin until the recessed cavity on the reverse side of the convex bearing head is in contact with the mounting plate. A fixing screw includes an axial bore configured so as to permit the fixing screw to pass over the guide pin. The fixing screw can be tightened using a cannulated hexagonal screw driver. Once the fixing screw is engaged in the threaded bore within the mounting plate central pin the guide pin can be removed before fully tightening the screw. The screw is preferably tightened until the scapula begins to rotate in response to motion of the screw driver.

Figure 28:
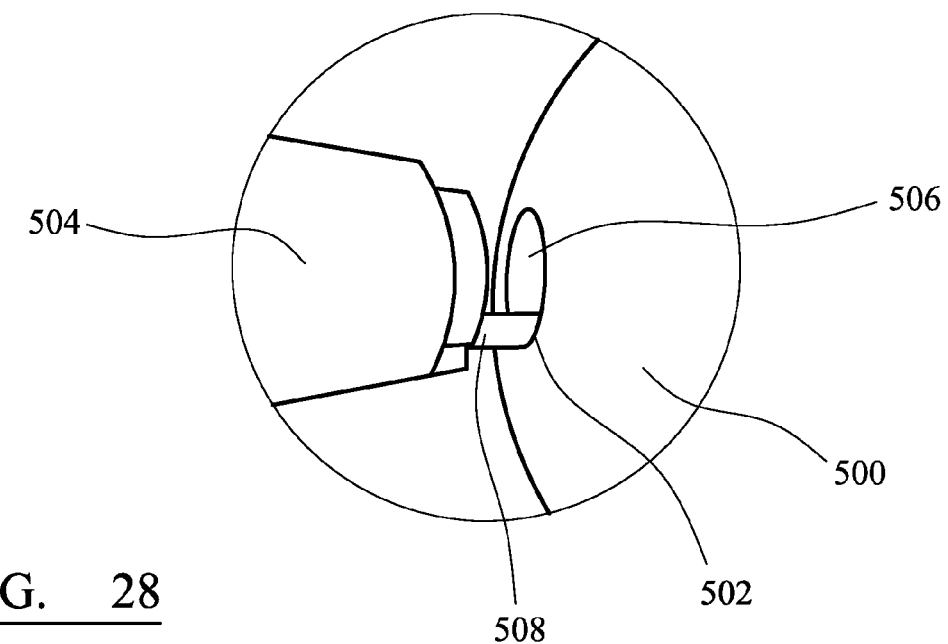
FIG. 28 illustrates part of a convex bearing head forming part of a reverse shoulder prosthesis and part of a convex bearing head orientation guide for correctly aligning the eccentricity of the convex bearing head.
Figure 31:
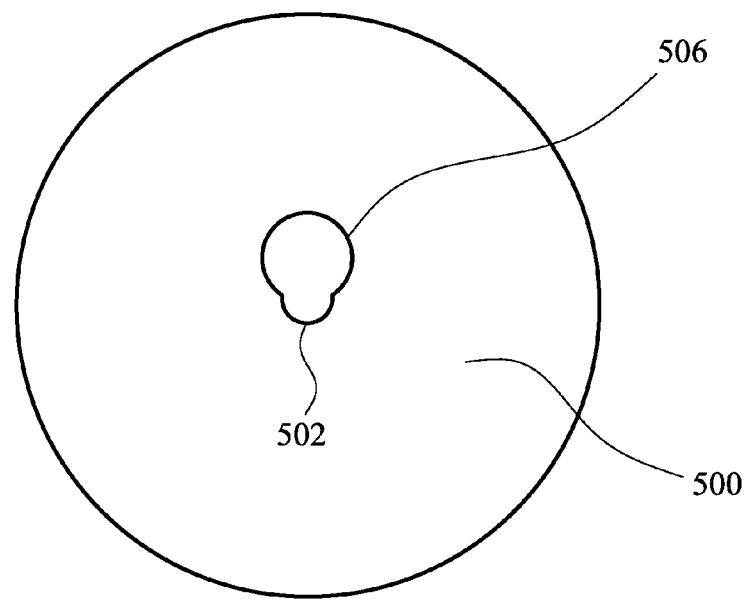
FIG. 31 illustrates a front view of the convex bearing head of FIG. 28.

For an eccentric convex bearing head, it is important that the eccentricity is in the correct radial position. The maximum eccentricity should be directed towards the base of the glenoid. Referring to FIG. 28, in order to rotate the convex bearing head upon the mounting plate the convex surface of the convex bearing head 500 incorporates a reference formation 502. The reference formation 502 can be manipulated by a convex bearing head orientation guide 504, which is arranged to slide over the screw driver. As shown in FIG. 28, the reference formation 502 comprises an eccentric slot enlarging part of the fixation hole 506. The fixation hole 506 including slot 502 is shown more clearly in a front view of the convex bearing head 500 in FIG. 31. The convex bearing head orientation guide 504 includes a pin 508 which protrudes from the body of the guide 504 and is configured to be received within the slot 502. The orientation guide 504 may further comprise a circular guide arranged to be received within the fixation hole 506. The screw driver is passed through the guide 504 and engages the fixing screw within fixation hole 506. The convex bearing head 500 can be rotated about the fixation hole 506 by manipulating the body of the convex bearing head orientation guide 504 while tightening the fixing screw.

Figure 29:
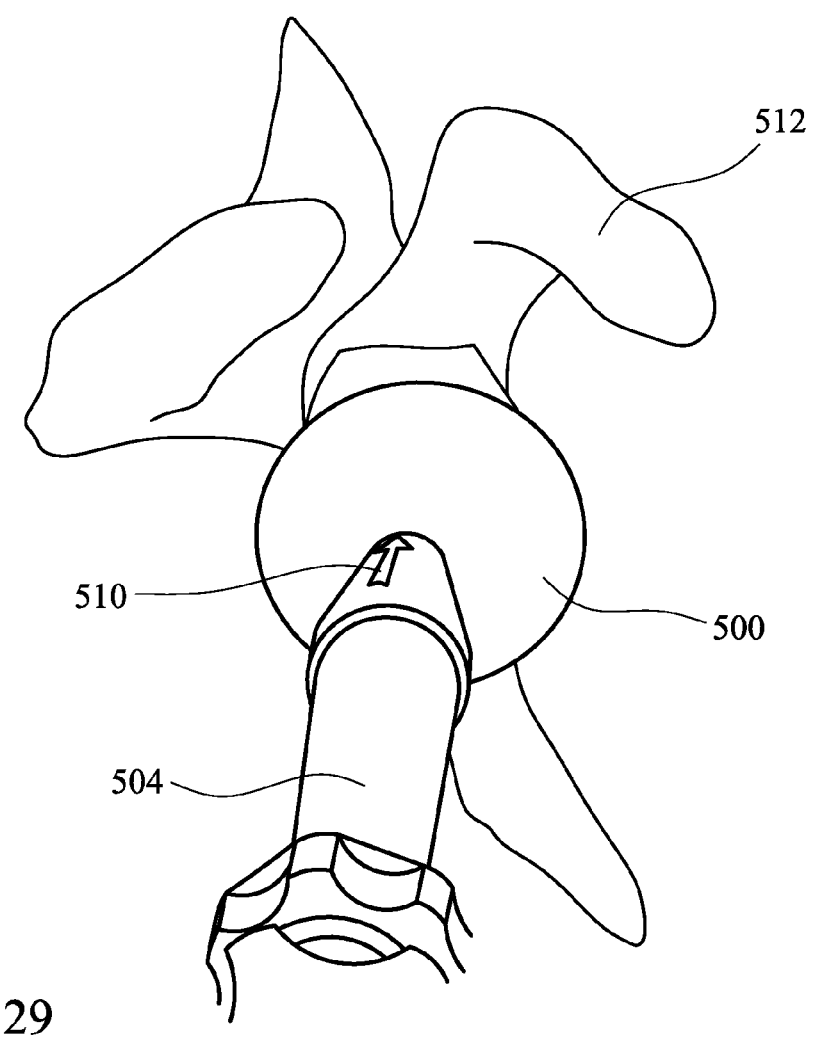
FIG. 29 illustrates the convex bearing head and convex bearing head orientation guide of FIG. 28 during attachment of the convex bearing head to a glenoid.

Referring to FIG. 29, the outside surface of the convex bearing head orientation guide 504 preferably includes an arrow 510. The correct rotation position of the convex bearing head 500 can be achieved by rotating the convex bearing head orientation guide 504 (and hence the convex bearing head 500) until the arrow 510 is aligned with a predetermined part of the scapula 512. For instance, if the required radial position of maximum eccentricity is towards the inferior portion of the glenoid, the reference formation 502 (which is aligned with the maximum eccentricity) should also point to the inferior portion of the glenoid. The arrow 510 is on the opposite side of the orientation guide 504 from the pin 508 and should be aligned with the superior portion of the glenoid. In particular, the convex bearing head 500 and the orientation guide 504 should be rotated until the arrow 510 points to the base of the coracoid process in order to correctly align the convex bearing head before tightening the fixing screw while maintaining the guide 504 in position. The convex bearing head may be further secured to the mounting plate by applying an impaction force to the convex bearing head and then further tightening the fixing screw.

It will be apparent to the skilled person that in alternative embodiments the reference formation may differ from that illustrated in FIG. 28, for instance it could be a different shape or may not be formed together with the fixation hole.

Figure 30:
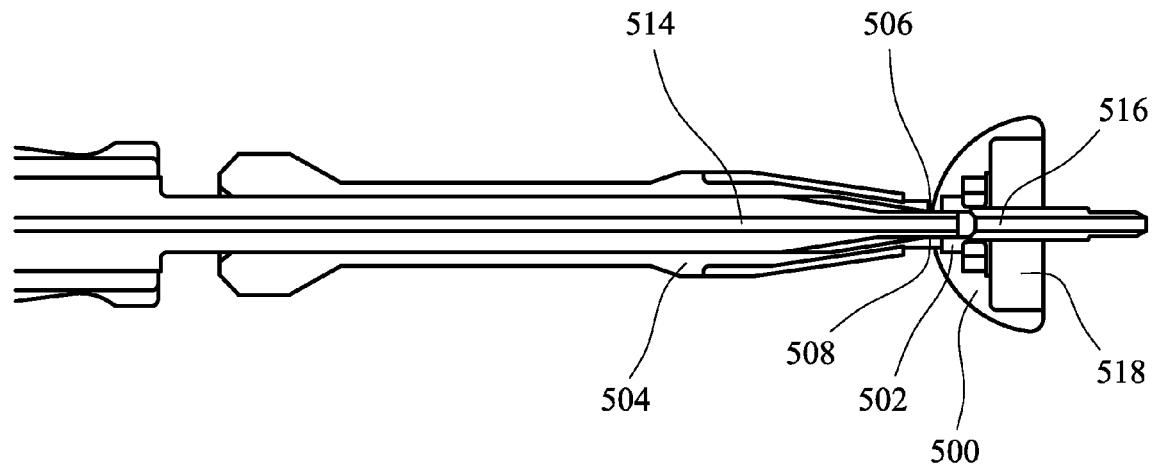
FIG. 30 illustrates the orientation guide of FIG. 29 in cross section along its longitudinal axis during attachment of the convex bearing head to a glenoid, including a screwdriver passing through a central bore of the orientation guide.

Referring to FIG. 30, this illustrates a cross section view of the orientation guide 504 engaged with the convex bearing head 500. Guide pin 508 is received within slot 502 within the fixation hole 506. A screw driver 514 is shown extending through an axial lumen within the orientation guide 504 to engage fixing screw 516 which secures the convex bearing head 500 to the mounting plate 518. In alternative embodiments in which the reference formation is not combined with the fixation hole, the alignment guide and the screwdriver may be provided separately.

The reverse shoulder prosthesis is completed by positioning a cup in a recess in the upper surface of the epiphysis. The cup presents a concave bearing surface in which the convex bearing head is received. The size of the cup (for example, 38 mm or 42 mm in diameter) is chosen to match the size of the convex bearing head. Additionally, the cup is available in a range of thicknesses. The cup thickness chosen is dependent upon the precise positioning of the resection surface and the mounting plate. If the implanted prosthesis results in an insufficiently tensioned shoulder joint (in which the joint tends to dislocate during motion) then a thicker cup may be used to increase the tension by increasing the distance between the scapula and the humerus.

It can be necessary to change the humeral component to the anatomic configuration (and also to change the glenoid component to the anatomic configuration). This may either be during a revision procedure due to glenoid loosening or during the initial surgical procedure to implant the prosthesis if it becomes apparent that there is insufficient glenoid bone stock to attach the mounting plate after the point at which the humerus has been resected.

In order to change the humeral component to the anatomic configuration it is necessary to remove cortical bone in the medial and lateral regions around the humeral head. This is because the anatomic head to be fitted to the implanted humeral implant overlaps the cortical bone in these regions. It is important to minimize any disturbance the humeral stem during this bone preparation stage.

The first step is to remove the humeral cup from the epiphysis. A reaming guide 600 can then be inserted into the cavity within the epiphysis 602 as shown in FIG. 32 and connected to the existing epiphysis 602 by a taper junction. That is, the epiphysis 602 comprises a shallow cavity formed generally as a portion of a cone. The sides of the open cavity formed in the epiphysis 602 diverge towards the open end. Similarly, the reaming guide 600 generally comprises a disc having tapering edges arranged to match the taper of the epiphysis open cavity. The taper junction forms a firm connection between the epiphysis 602 and the reaming guide 600 during reaming of the bone, while allowing the reaming guide 600 to removed later. The reaming guide 600 comprises two sockets 604 that define reaming axes. The reaming axes diverge as they extend from the epiphysis 602. The reaming guide 600 is positioned in the epiphysis 602 such that anterior and posterior slots 606 are aligned with corresponding slots 608 in the rim of the epiphysis 602. The reaming guide 600 forms a press fit with the epiphysis component cup temporarily securing guide 600 in position. The reaming axes are directed medially and laterally.

As shown in FIG. 33, an appropriate reaming head 610 is driven about an axial guide 615 that is arranged to be inserted into socket 604. The reaming head 610 is driven by a means (not shown) to remove cortical bone in the lateral (or medial, depending on the chosen axis) direction without contacting the implanted stem component. The reaming head 610 comprises a reaming ring 612 that is configured to pass around the epiphysis 602 contacting the cortical bone immediately surrounding the epiphysis 602 predominantly in the medial (or lateral) direction. Reaming ring 612 is driven radially about axial guide 615 to remove bone on the proximal portion of the humerus.

As shown in FIG. 34, once bone is removed on the medial and/or lateral portions of the humerus, an appropriately sized humeral head implant 614 is secured to the epiphysis forming a press fit in the epiphysis cavity overlapping the epiphysis and the cortical bone in the medial and lateral directions.

Although surgical instruments and techniques described above are primarily related to a reverse shoulder prosthesis implantation procedure it will be appreciated that some or all of the surgical instruments and surgical techniques described may be equally applicable elsewhere. For instance, they may find utility in the implantation of other prostheses, such as a hip prosthesis. Additionally, some or all of the surgical instruments and techniques described may be equally applicable to the implantation of anatomic prostheses as opposed to reversed anatomy prostheses.

Other modifications and applications of the present invention will be readily apparent from the description herein without departing from the scope of the appended claims.

The invention claimed is:

1. A method of reaming bone around a head of a bone, the bone including an implanted epiphysis component having an upper surface, an outer perimeter and a cavity extending from the upper surface in a distal direction, the method comprising the steps of:
   coupling a reaming guide to the implanted epiphysis component,
   coupling a reamer to the reaming guide; and
   reaming bone around at least a portion of the outer perimeter and below the upper surface of the implanted epiphysis component using the reamer,
   wherein the reamer guide has a first socket extending into the reamer guide along a first axis, and a second socket extending into the reamer guide along a second axis, and the reamer comprises an axial guide sized and shaped to be at least partially disposed within one of the first socket and the second socket, the method further comprising the step of inserting the reamer protrusion into one of the first socket and the second socket such that the reamer is held in a fixed spatial relationship with the reaming guide during the reaming step.

2. The method of claim 1, wherein the first axis and the second axis diverge from one another, and the reamer further comprises a reaming head extending about the axial guide, wherein the reaming step comprises reaming bone around the epiphysis component in a concentric ring about the first axis or the second axis.

3. The method of claim 1, wherein a first portion of the reaming guide is generally disc-shaped and is sized and shaped to connect to the cavity of the implanted epiphysis component, and the coupling step comprises inserting the first portion of the reaming guide into the cavity of the implanted epiphysis component.

4. The method of claim 3, wherein the reaming guide further comprises an alignment feature, the method further comprising the step of aligning the alignment feature with a corresponding implanted epiphysis component alignment feature.

5. The method of claim 3, wherein the first portion of the reaming guide and the implanted epiphysis component are coupled by way of a taper lock.

6. The method of claim 1, wherein the reaming guide comprises a generally disc-shaped first portion of the reaming guide and a second portion extending proximally from the first portion, and wherein the first socket extends into the second portion of the reamer guide at a location spaced apart from the upper surface of the implanted epiphysis component and a second socket extends into the second portion of the reamer guide a location spaced apart from the upper surface of the implanted epiphysis component.

7. The method of claim 2, wherein the inserting step further comprises the step of inserting the reamer protrusion into the other of the first socket and the second socket such that the reamer is held in a fixed spatial relationship with the reaming guide during the reaming step, and wherein the reaming step further comprises reaming about one of the first axis or the second axis and then reaming about the other of the first axis or the second axis.

8. The method of claim 1, further comprising the step of securing a humeral head implant to the implanted epiphysis component.

* * * * *